(12) United States Patent
Creech et al.

(10) Patent No.: US 7,141,419 B2
(45) Date of Patent: Nov. 28, 2006

(54) ISOLATED NUCLEIC ACIDS ENCODING CYCLIC NUCLEOTIDE-GATED CATION CHANNEL SUBUNIT 3B (CNG3B) POLYPEPTIDES

(75) Inventors: Christopher D. Creech, Garner, NC (US); Timothy J. Jegla, San Diego, CA (US)

(73) Assignee: Icagen, Inc., Durham, NC (US)

( * ) Notice: Subject to any disclaimer, the term of this patent is extended or adjusted under 35 U.S.C. 154(b) by 530 days.

(21) Appl. No.: 09/855,828

(22) Filed: May 14, 2001

(65) Prior Publication Data

US 2004/0137433 A1 Jul. 15, 2004

Related U.S. Application Data

(60) Provisional application No. 60/204,445, filed on May 15, 2000.

(51) Int. Cl.
- C12N 5/10 (2006.01)
- C12N 15/12 (2006.01)
- C12N 15/63 (2006.01)
- C12N 1/21 (2006.01)

(52) U.S. Cl. .............. 435/325; 435/252.3; 435/320.1; 435/69.1; 536/23.5

(58) Field of Classification Search ............ 435/252.3, 435/254.11, 320.1, 325; 530/350; 536/23.1, 536/23.5, 24.3
See application file for complete search history.

(56) References Cited

OTHER PUBLICATIONS

Bork. (2000). Power and pitfalls in sequence analysis: the 70% hurdle. Genome Research 10:398-400.*
Finn et al. (1996). Cyclic nucleotide-gated eion channels: an extended family with diverse functions. Ann. Rev. of Physiol. 58:395-426.*
Ngo et al. (1990). Computational complexity, protein structure prediction, and the Levinthal paradox. In Merz and Le Grand (Eds.) The Protein Folding Problem and Tertiary Structure Prediction. Birkhauser:Boston.*
Wells, J.A. (1990). Addivity of mutational effects in proteins. Biochemistry 29:8509-8517.*
Skolnick et al. (2000). From genes to protein structure and function: novel applications of computational approaches in the genomic era. Trends in Biotech. 18:34-39.*
Kramer et al. (2001). Modulation of cyclic-nucleotide-gated channels and regulation of vertebrate phototransduction. The Journal of Experimental Biology. 204:2921-2931.*
Peng et al. (2003). Achromatopsia-associated mutation in the human cone photoreceptor cyclic nucleotide-gated channel CNG3B subunit alters the ligand sensitivity and pore properties of heteromeric channels. J. Biol. Chem. 278(36):34533-34540.*
Broillet et al. (1999). Cyclic nucleotide-gated channels. Molecular mechanisms of activation. Annals New York Academy of Sciences. 868:730-40.*
Gerstner, et al., "Molecular Cloning and Functional Characterization of a New Modulatory Cyclic Nucleotide-Gated Channel Subunit from Mouse Retina"; *The Journal of Neuroscience*, 20(4):1324-1332 (Feb. 2000).
Kohl, et al., "Mutations in the CNGB3 gene encoding the β-subunit of the cone photoreceptor cGMP-gated channel are responsible for achromatopsia (ACHM3) linked to chromosome 8q21"; *Human Molecular Genetics*, vol. 9, No. 14 2107-2116 (2000).
Sundin, et al. "Genetic basis of total colourblindness among the Pingelapese islanders"; *Nature Genetics*, vol. 25, 289-293 (Jul. 2000).
Vinós, et al., "A G Protein-Coupled Receptor Phosphatase Required for Rhodopsin Function" *Science* vol. 277, 687-690 (Aug. 1997).
Gerstner, Andrea et al.; "Molecular Cloning and Functional Characterization of a New Modulatory Cyclic Nucleotide-Gated Channel Subunit from Mouse Retina"; 2000, *The Journal of Neuroscience*, vol. 20, No. 4, pp. 1324-1332.
Database EMBL, Jul. 6, 2000, retrived from EMBL Database accession No. AF228520.

* cited by examiner

*Primary Examiner*—Christine J. Saoud
*Assistant Examiner*—Jon M Lockard
(74) *Attorney, Agent, or Firm*—Townsend and Townsend and Crew, LLP

(57) ABSTRACT

The invention provides isolated nucleic acid and amino acid sequences of CNG3B, antibodies to CNG3B, methods of detecting CNG3B, and methods of screening for modulators of cyclic nucleotide-gated ion channels using biologically active CNG3B. The invention further provides, in a computer system, a method of screening for mutations of human CNG3B genes as well as a method for identifying a three-dimensional structure of human CNG3B polypeptides.

5 Claims, 9 Drawing Sheets

FIG. 1.

```
410  GLFEPQTLFEIVFQLLNFESGVEVFSSLIGQMRDVIGAATANQNYFRACMDDTIAYMNNY  Cng3BFL.pro
368  ETPPVKDEEYLFVVVDFLFGVLIFATIVGNVGSMISNMNASRAEFQAKIDSIKQYMQFR  CNGA3.pro
365  ETPPVRDSEYVFVVVDFLIGVLIFATIVGNIGSMISNMNAARAEFQARIDALKQYMHER  CNGA1.pro 470  SIPKLVQKRVRTWYEYIWDSQRMLDSDLIKTIETTVQLALAIDVNFSIISKVDLFKGCD  Cng3BFL.pro
428  KVTKDLEFRVIRWFDYLWANKKTVDEKEVLKSLPDKLKAEIAINVHLDTLKKVRIFQDCE  CNGA3.pro
425  NVSKDMEKRVIKWFDYLWTNKKTVDEKEVLKYLPDKLRAEIAINVHLDRLKKVRIEADCE  CNGA1.pro 530  TQMIYDMIFEIKSVIINLPGDEVCKKGEIGKEMYIIKHGEVQLGGPDGTKVIMIIKAGSV  Cng3BFL.pro
488  AGLLVELVLKIRPTVESPGDYICKKGDIGKEMYIINEGKLAVVAD-DGVTQFVVLSDGSY  CNGA3.pro
485  AGLLVELVLKIQPQVYSPGDYICKKGDIGREMYIIKEGKLAVVAD-DGVTQFVVLSDGSY  CNGA1.pro 590  FGEISLIIAAGG----GNRRTANVVAHGEANILTDKTIQFIIVHPDSERIIMKRARIVL  Cng3BFL.pro
547  FGEISILNIKGSKSGNRRTANIRSIGYSDLFCLSKDDLMEALTEYPEAKKALEEKGRQIL  CNGA3.pro
544  FGEISILNIKGSKAGNRRTANIKSIGYSDLFCLSKDDLMEALTEYPDAKTMLEEKGRQIL  CNGA1.pro 646  IKQKAKTAEATPPRKDLALLFPPKEETKRLFKILLGGTGKASLARLLKIKREQAAQKKEN  Cng3BFL.pro
607  MKDNIIDEEIARAGAD------PKDLEEKV--EQLGSSLDTLQTREFARLL--------  CNGA3.pro
604  MKDGLIDLNTANAGSD------PKDLEEKV--IRMEGSVDLLQTREFARLL--------  CNGA1.pro 706  SEGGEEEGKENEDKQKENEDKGRENEDKGREPEEKPLDRPECTASPIAVEEBIADGE  Cng3BFL.pro
649  ---AEYNATOMKMKQRISQLESQVKGGGDK----------------EFSSIE  CNGA3.pro
646  ---AEYESMQQKIKQRLTKVEKFLKPLIDT----------------EFSSIE  CNGA1.pro 766  EPHSVRRTVLPRGTSRQSLLIISMAPSAEGGEEVLTIEVKEKAKQ.  Cng3BFL.pro
682  VP----------------------------GDATKTED----KQQ.  CNGA3.pro
679  GP----------------------------GAESGPID----ST.  CNGA1.pro
```

FIG. 1. (CONTINUED)

```
CCATCCTAATACGACTCACTATAGGGCTCGAGCGGCCGCCCGGGCCAGGTCATTTCTCTACCTTAAGGCACAGTCATA
AATACAGAGGGTTTCAGAACCACCTCAGAGAAGATGTTTAAATCGCTGACAAAGTCAACAAGGTGAAGCCTATAG
GAGAGAACAATGAGAATGAACAAAGTTCTCGTCGGAATGAAGAAGGCTCTCACCCAAGTAATCAGTCTCAGCAAACC
ACAGCACAGGAAGAAAACAAAGGTGAAGAGAAATCTCTCAAAACCAAGTCAACTCCAGTCACGTCTGAAGAGCCACA
CACCAACATACAAGACAAACTCTCCAAGAAAAATTCCTCTGGAGATCTGACCACAAACCCTGACCCTCAAAATGCAG
CAGAACCAACTGGAACAGTGCCAGAGCAGAAATGGACCCCCGGGAAAGAAGGTCCAAACAGCCCACAAAACAAA
CCGCCTGCAGCTCCTGTTATAAATGAGTATGCCGATGCCCAGCTACACAACCTGGTGAAAAGAATGCGTCAAAGAAC
AGCCCCTCTACAAGAGTAAAAGAAAGCGATGATAAGCCAACAGAACATTACTACAGGCTGTTGTGGTTCAAAGTCAAAAAG
CTGTACCACCAGTAAAAGAAGAGTACTTAAAGCGAATTAAACTTCCAAACAGCATAGATTCATACACAGATCGACTCTATCTCCT
ATGCCTTTAACAGAGTACTTAAAGCGAATTAAACTTCCAAACAGCATAGATTCATACACAGATCGACTCTATCTCCT
GTGGCTCTTGCTTGTCACTCTTGCCTATAACTGGAACTGCTGGTTTATACCACTGCGCCTCGTCTTCCCATATCAAA
CCGCAGACAACATACACTGGCTTATTGCGGACATCATATGTGATATCATCTACCTTTATGATATGCTATTTATC
CAGCCCCAGACTCCAGTTTGTAAGAGGAGGAGACATAATAGTGGATTCAAATGAGCTAAGGAAACACTACAGGACTTC
TACAAAATTTCAGTGTGGATGTCGCATCAATAATACCATTGATATTTGCTACCTCTTCTTTGGGTTTAATCCAATGT
```

FIG. 2.

```
TTAGAGCAAATAGGATGTTAAAGTACACTTCATTTTTTGAATTAATCATCACCTAGAGTCTATAATGGACAAAGCA

TATATCTACAGAGTTATTCGAACAACTGGATACTTGCTGTGTTTATTCTGCACATTAATGCCTGTGTTATTACTGGGC

TTCAAACTATGAAGGAATTGGCACTACTAGATGGGTGGTATGATGGGGAAGGAAACGAGTATCTGAGATGTTATTATT

GGGCAGTTCGAACTTTAATTACCATTGGTGTGGCCCTTCCAGAACCACAAACTTTATTTGAAATTGTTTTCAACTCTTG

AATTTTTTTCTGGAGTTTTTGTGTTCTCCAGTTTAATTGGTCAGATGAGAGATGTGATTGGAGCAGCTACAGCCAA

TCAGAACTACTTCCGCGCCCTGCATGGATGACACCATTGCCTACATGAACAATTACTCCATTCCTAAACTTGTGCAAA

AGCGAGTTCGGACTTGGTATGAATATACATGGGACTCTCAAAGAATGCTAGATGAGTCTGATTGCTTAAGACCCTA

CCAACTACGGTCCAGTTAGCCCTCGCCATTGATGTGAACTTCAGCATCATCAGCAAAGTCGACTTGTTCAAGGGTTG

TGATACACAGATGATTATGACATGTTGCTAAGATTGAAATCCGTTCTCTATTTGCCTGGACTTTGTCTGCAAAA

AGGGAGAAATTGGCAAGGAAATGTATATCATCAAGCATGGAGAAGTCCAAGTTCTTGGAGGCCCTGATGGTACTAAA

GTTCTGGTTACTCTGAAAGCTGGGTCGGGTTTGCCAATCTTTTAACTCTAGACAAAAAGACCCTCCAGCAGCAGACC

TGCCAATGTGGTGGCCACGGGTTTGCCACGGGTTTGCCAATCTTTTAACTCTAGACAAAAAGACCCTCCAAGAAATTCTAGTGCATT

ATCCAGATTCTGAAAGGATCCTCATGAAGAAGCCAGAGTGCTTTAAAGCAGAAGGCTAAGACCGCAGAAGCAACC

CCTCCAAGAAAAGATCTTGCCCTCCTCTTCCCACCGAAAGAAGAGACACCCAAACTGTTTAAAACTCTCCTAGGAGG
```

FIG. 2. (CONTINUED)

```
CACAGGAAAAGCAAGTCTTGCAAGACTACTCAAATTGAAGCGAGAGCAAGCAGCTCAGAAGAAAGAAAATTCTGAAG
GAGGAGAGGAAGAAGGAAAAGAAAATGAAGAGATAAACAAAAAGAAAATGAAGATAAAGAAAATGAAGATAAA
GGAAAAGAAAATGAAGATAAAGAAGAGAGAAGAGAGCCACTGGACAGACCTGAATGTACAGCAAG
TCCTATTGCAGTGGAGGAAGAACCCCACTCAGTTAGAGGACAGTTTTACCCAGAGGACTTCTCGTCAATCACTCA
TTATCAGCATGGCTCCTTCTGCTGAGGGCGAGAGAGGTTCTTACTATTGAAGTCAAAGAAAAGGCTAAGCAATAA
ATGTTTGATTATCTTTAGATGTGATATAGCTAGTTCCCAAAGTGATTGTACCTAGGATTGTAACTTAAATTAACGAG
GGGAAACGACATGCTGGGACCCTTGAGAAACGAAAGGCAAATCCCTAGCTTAGTTTCTAGGACTTATCTGAGAGTGT
GATTTCATGCAGTGGTAATAAGAAGATTATTAAAGCAAAAAAAAAAAAAAAAAAAAA
```

FIG. 2. (CONTINUED)

ATGTTTAAATCGCTGACAAAGTCAACAAGGTGAAGCCTATAGGAGAGAACAATGAGAATGAACAAAGTTCTCGTCGGAA

TGAAGAAGGCTCTCACCCAAGTAATCAGTCTCAGCAAACCACAGCAAGAAAACAAAGGTGAAGAGAGAAATCTCTCA

AAACCAAGTCAACTCCAGTCACGTCTGAAGAGCCACACACCAACATACAAGACAAACTCTCCAAGAAAAATTCCTCTGGA

GATCTGACCACAAACCCTGACCCTCAAAATGCAGCAGAACCAACTGGAACAGTGCCAGAGCAGAAGGAAATGGACCCGG

GAAAGAAGGTCCAAACAGCCCACAAAACAAACCGCCTGCAGCTCCTGTTATAAATGAGTATGCCGATGCCCAGCTACACA

ACCTGGTGAAAAGAATGCGTCAAAGAACAGCCCCTCTACAAGAAAAAGTTGGTAGAGGGAGATCTCTCCTCACCCGAAGCC

AGCCCACAAACTGCAAAGCCCACGGCTGTACCACCAGTAAAAAGAAAGCGATGATAAGCCAACAGCATAGATTCATATACA

GTTGTGGTTCAAAGTCAAAAAGATGCCTTTAACAGAGTACTTAAAGCGAATTAAACTTCCAAACAGCAGCCTGCGCCTC

CAGATCGACTCTATCTCCCTGTGGCCTCTGTGCTCTTGCTCACTCCTTGCCTATAACTGGAACTGCTGTGTTATACCACTGCGCCTC

GTCTTCCCATATCAAACCGCAGACAACATACACTGGCTTATTGCGGACATCATATGTGATATCATCTACCTTTATGA

TATGCTATTTATCCAGCCCAGACTCCAGTTTGTAAGAGGAGACATAATAGTGGATTCAAATGAGCTAAGGAAACACT

ACAGGACTTCTACAAAATTTCAGTTGGATGTGCATCAATAATACCATTTGATATATTGCTACCTCTTCTTGGGTTTAAT

CCAATGTTTAGAGCAAATAGGATGTTAAAGTACACTTCATTTTTGAATTTAATCATCACCTAGAGTCTATAATGGACAA

AGCATATATCTACAGAGTTATTCGAACAACTGGATACTTGCTGTTTATTCTGCACATTAAATGCCTGTGTTTATTACTGGG

FIG. 3.

CTTCAAACTATGAAGGAATTGGCACTACTAGATGGGTGTATGATGGGAAGGAAACGAGTATCTGAGATGTTATTATTGG

GCAGTTCGAACTTTAATTACCATTGGTGGCCCTTCCAGAACCACAAACTTTATTTGAAATTGTTTTCAACTCTTGAATTT

TTTTTCTGGAGTTTTGTGTTCTCCAGTTTAATTGGTCAGATGAGAGATGTGATTGGAGCAGCTACAGCCAATCAGAACT

ACTTCCGCGCCTGCATGGATGACACCATTGCCTACATGAACAATTACTCCATTCCTAAACTTGTGCAAAAGCGAGTTCGG

ACTTGGTATGAATATACATGGGACTCTCAAAGAATGCTAGATGAGTCTGATTTGCTTAAGACCCTACCAACTACGGTCCA

GTTAGCCCCTCGCCATTGATGTGAACTTCAGCATCATCAGCAAAGTCGACTTGTTCAAGGGTTGTGATACACAGATGATTT

ATGACACATGTTGCTAAGATTGAAAATCCGTTCTCTATTGCCTGGTGACTTTGTCTGCAAAAAGGGAGAAATTGGCAAGGAA

ATGTATATCATCAAGCATGGAGAAGTCCAAGTTCTTGGAGGCCCTGATGGTACTAAAGTTCTGGTTACTCTGAAAGCTGG

GTCGGGTGTTTGGAGAAATCAGCCTTCTAGCAGGAGGAGGAAACCGTCGAACTGCCAATGTGGTGGCCACGGGTTTG

CCAATCTTTTAACTCTAGACAAAAAGACCCTCCAAGAAATTCTAGTGCATTATCCAGATTCTGAAAGGATCCTCATGAAG

AAAGCCAGAGTGCTTTTAAAGCAGAAGGCTAAGACCGCAGAAGCAACCCCTCCAAGAGAAAAGATCTTGCCCTCCTCTTCCC

ACCGAAAGAAGAGACACCCAAACTGTTTAAAACTCTCCTAGGAGGCACAGGAAAAGCAAGTCTTGCAAGACTACTCAAAT

TGAAGCGAGAGCAAGCAGCTCAGAAGAAAAGAAAATTCTGAAGGAGGAGAGGAAGAAGGAAAAGAAAATGAAGATAAACAA

AAAGAAAAATGAAGATAAACAAAAAGAAAAATGAAGATAAAGGAAAAGATAAAGATAAAGGAAGAGAGCCAGA

FIG. 3. (CONTINUED)

AGAGAAGCCACTGGACAGACCTGAATGTACAGCAAGTCCTATTGCAGTGGAGGAAGAACCCCACTCAGTTAGAAGGACAG

TTTTACCCAGAGGGACTTCTCGTCAATCACTCATTATCAGCATGGCTCCTTCTGCTGAGGGCGGAGAAGAGGTTCTTACT

ATTGAAGTCAAAGAAAAGGCTAAGCAATAA

FIG. 3. (CONTINUED)

MFKSLTKVNKVKPIGENNENEQSSRRNEEGSHPSNQSQQTTAQEENKGEEKSLKTKSTPVTS
EEPHTNIQDKLSKKNSSGDLTTNPDPQNAAEPTGTVPEQKEMDPGKEGPNSPQNKPPAAPVI
NEYADAQLHNLVKRMRQRTALYKKKLVEGDLSSPEASPQTAKPTAVPPVKESDDKPTEHYYR
LLWFKVKKMPLTEYLKRIKLPNSIDSYTDRLYLLWLLLVTLAYNWNCWFIPLRLVFPYQTAD
NIHYWLIADIICDIIYLYDMLFIQPRLQFVRGGDIIVDSNELRKHYRTSTKFQLDVASIIPF
DICYLFFGFNPMFRANFMLKYTSFFEFNHHLESIMDKAYIYRVIRTTGYLLFILHINACVYY
WASNYEGIGTTRWVYDGEGNEYLRCYYWAVRTLITIGGLPEPQTLFEIVFQLLNFFSGVFVF
SSLIGQMRDVIGAATANQNYFRACMDDTIAYMNNYSIPKLVQKRVRTWYEYTWDSQRMLDES
DLLKTLPTTVQLALAIDVNFSIISKVDLFKGCDTQMIYDMLLRLKSVLYLPGDFVCKKGEIG
KEMYIIKHGEVQVLGGPDGTKVLVTLKAGSVFGEISLLAAGGNRRTANVVAHGFANLLTLD
KKTLQEILVHYPDSERILMKKARVLLKQKAKTAEATPPRKDLALLFPPKEETPKLFKTLLGG
TGKASLARLLKLKREQAAQKKENSEGGEEEGKENEDKQKENEDKGKENEDKDKGR
EPEEKPLDRPECTASPIAVEEEPHSVRRTVLPRGTSRQSLIISMAPSAEGGEEVLTIEVKEK
AKQ

FIG. 4.

ISOLATED NUCLEIC ACIDS ENCODING CYCLIC NUCLEOTIDE-GATED CATION CHANNEL SUBUNIT 3B (CNG3B) POLYPEPTIDES

CROSS-REFERENCES TO RELATED APPLICATIONS

The present application claims priority to U.S. Ser. No. 60/204,445, filed May 15, 2000, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The invention provides isolated nucleic acid and amino acid sequences of CNG3B, antibodies to CNG3B, methods of detecting CNG3B, and methods of screening for modulators of cyclic nucleotide-gated cation channels using biologically active CNG3B. The invention further provides, in a computer system, a method of screening for mutations of human CNG3B genes as well as a method for identifying a three-dimensional structure of human CNG3B polypeptides.

BACKGROUND OF THE INVENTION

Cyclic nucleotide gated cation channels (CNG) are a class of non-selective cation channels that are opened by direct binding of cyclic nucleotides such as cGMP and cAMP. CNG channels are highly permeable to $Na^+$ and $Ca^{2+}$, and their activation leads to depolarization and increases in internal $Ca^{2+}$ concentrations. These channels can link changes in cytoplasmic cyclic nucleotide levels to changes in cellular excitability, secretion of neurotransmitters and the stimulation of calcium-dependent pathways.

CNG family channel proteins are multimers and can be formed by at least two functionally distinct classes of subunits. The two classes of subunits, alpha and beta, share a common motif of 6 transmembrane domains, a pore motif and a cytoplasmic cyclic nucleotide binding domain (Finn et al, *Annu. Rev. Physiol.* 58:395–426:1996). CNG alpha subunits can form functional channels as homomultimers, i.e., all subunits contributing to the channel pore are identical. Beta subunits, in contrast, can only form functional channels when expressed with an alpha subunit. These heteromultimeric channels show functional properties consistent with native CNG channels (Gerstner, A., et al, *J. Neurosci.* 20(4):1324–1332, 2000; Finn J T, et al, *Annu. Rev. Physiol.* 58:395–426, 1996). For example, coexpression of alpha and beta subunits occurs in retinal rod cells where the alpha subunit CNGA1 forms a heteromultimer with the beta subunit CNGB1 (CNG4) (Gerstner, A., et al, *J. Neurosci.* 20(4):1324–1332, Feb. 15, 2000).

CNG channels are important for sensory signal transduction in retinal and olfactory and taste bud cells in response to primary sensory stimuli such as light and aerosolized or dissolved molecules (Ding, C, et al, *Am. J. Physiol.* 272 (*Cell Physiol.* 41): C1335–C1344, 1997). In photoreceptor cells, CNG channels are open in darkness due to a high basal concentration of cGMP. This causes a tonic depolarization of the membrane and constitutive neurotransmitter release. Upon stimulation by light, cGMP levels drop, closing the CNG channels. This in turn causes a hyperpolarization of the membrane, a drop in the internal $Ca^{2+}$ concentration, and a decrease in the release of neurotransmitter (Finn, J T, et al, *Annu. Rev. Physiol.* 58:395–426, 1996).

CNG channels have been found in a number of tissues, suggesting that these channels may link a variety of stimuli to changes in membrane potential and cytoplasmic calcium levels (Ding, C, et al, *Am. J. Physiol.* 272 (*Cell Physiol.* 41):C1335–C1344, 1997; Kingston P, *Synapse* 32:1–12, 1999). For instance, retinal and olfactory CNG channels are expressed in various parts of the brain (Ding, C, et al, *Am. J. Physiol.* 272 (*Cell Physiol.* 41):C1335–C1344, 1997; Kingston P, *Synapse* 32:1–12, 1999). Because these channels are highly permeable to $Ca^{2+}$, they may stimulate $Ca^{2+}$-dependent pathways that have significant effects on neuronal activity. More directly, they may contribute to neuronal activity by providing excitatory depolarizations. CNG channels may also interact with other second messenger systems such as the Nitric Oxide-pathway to provide the longer lasting changes that are important mechanisms in learning and memory (Kingston P, *Synapse* 32:1–12, 1999). CNG channels have been found in the testis, and through the regulation of the internal $Ca^{2+}$ concentration, may be involved in chemotaxis of sperm (Weyand, I., et al, *Nature* 368:859–863, 1994). Expression of CNG channels has also been noted in heart, aorta and kidney, where they may play a role in the regulation of heart rate, blood pressure and electrolyte transport, respectively (Finn et al., *Ann. Rev. Physiol.* 1996, 58:395–426). The full scope of CNG channel function is not yet entirely understood, but it is clear that they play a key role in many physiological processes.

SUMMARY OF THE INVENTION

The current invention provides the first isolation and characterization of human CNG3B, a novel subunit of a cyclic nucleotide gated cation channel. The present invention provides both the nucleotide and amino acid sequence of CNG3B, as well as methods of assaying for modulators of CNG3B, antibodies to CNG3B, and methods of detecting CNG3B nucleic acids and proteins.

In one aspect, the present invention provides an isolated nucleic acid encoding a polypeptide comprising a subunit of a cation channel, the polypeptide: (i) forming, with at least one CNG alpha subunit, a cation channel having the characteristic of cyclic nucleotide-gating; and (ii) comprising a subsequence having at least 85% amino acid sequence identity to amino acids 210 to 661 of SEQ ID NO:1.

In one embodiment, the polypeptide specifically binds to antibodies generated against a polypeptide comprising an amino acid sequence of SEQ ID NO: 1. In another embodiment, the polypeptide encodes human CNG3B. In another embodiment, the nucleic acid encodes a polypeptide comprising an amino acid sequence of SEQ ID NO:1.

In one embodiment, the nucleic acid comprises a nucleotide sequence of SEQ ID NO:2 or SEQ ID NO:3. In another embodiment, the nucleic acid is amplified by primers that selectively hybridize under stringent hybridization conditions to the same sequence as the primers selected from the group consisting of:

| | |
|---|---|
| TCTATCTCCTGTGGCTCTTGCTTGTC | (SEQ ID NO: 4) |
| GAGTCTGGGCTGGATAAATAGCATATC | (SEQ ID NO: 5) |
| AGGAATTGGCACTACTAGATGGGTG | (SEQ ID NO: 6) |

-continued

| | |
|---|---|
| TTCATGAGGATCCTTTCAGAATCTGG | (SEQ ID NO: 7) |
| GGAAACCGTCGAACTGCCAATGTGGT | (SEQ ID NO: 8) |
| CGGGTTTGCCAATCTTTTAACTCTAGAC | (SEQ ID NO: 9) |
| GTCCGCAATAAGCCAGTAGTGTATG | (SEQ ID NO: 10) |
| TGACAAGCTTCCGCCATGTTTAAATCGCTGACAA AAGTC and | (SEQ ID NO: 11) |
| TGACGAATTCTCCCAGCATGTCGTTTCCCCTCGT TAA. | (SEQ ID NO: 12) |

In another embodiment, the polypeptide comprises a beta subunit of a heteromeric cyclic nucleotide gated cation channel. In another embodiment, the nucleic acid selectively hybridizes under moderately stringent hybridization conditions to a nucleic acid comprising a nucleotide sequence of SEQ ID NO:2 or SEQ ID NO:3.

In another aspect, the present invention provides an isolated nucleic acid encoding a CNG3B polypeptide, the nucleic acid specifically hybridizing under stringent conditions to a nucleic acid comprising a nucleotide sequence of SEQ ID NO:2 or SEQ ID NO:3.

In another aspect, the present invention provides an isolated nucleic acid that specifically hybridizes under stringent conditions to a nucleic acid encoding an amino acid sequence of SEQ ID NO:1.

In another aspect, the present invention provides a method of detecting a nucleic acid, the method comprising contacting the nucleic acid with an isolated nucleic acid, as described above.

In another aspect, the present invention provides expression vectors comprising the nucleic acids of the invention, and host cells comprising such expression vectors.

In another aspect, the present invention provides an isolated polypeptide comprising a subunit of a cation channel, the polypeptide: (i) forming, with at least one CNG alpha subunit, a cation channel having the characteristic of cyclic nucleotide-gating; and (ii) comprising a subsequence having at least 85% amino acid sequence identity to amino acids 210 to 661 of SEQ ID NO:1.

In one embodiment, the polypeptide specifically binds to antibodies generated against SEQ ID NO:1. In another embodiment, the polypeptide has a molecular weight of between about 87 kD to about 97 kD. In another embodiment, the polypeptide has an amino acid sequence of human CNG3B. In another embodiment, the polypeptide has an amino acid sequence of SEQ ID NO:1.

In one embodiment, the polypeptide comprises a beta subunit of a heteromeric cyclic nucleotide-gated cation channel.

In another aspect, the present invention provides an antibody that specifically binds to the CNG3B polypeptide described herein.

In one embodiment, the polypeptide to which the antibody binds has an amino acid sequence of SEQ ID NO:1.

In another aspect, the present invention provides a method for identifying a compound that increases or decreases ion flux through a cation channel, the method comprising the steps of: (i) contacting the compound with a CNG3B polypeptide, the polypeptide (a) forming, with at least one CNG alpha subunit, a cation channel having the characteristic of cyclic nucleotide-gating; and (b) comprising a subsequence having at least 85% amino acid sequence identity to amino acids 210 to 661 of SEQ ID NO:1; and (ii) determining the functional effect of the compound upon the cation channel.

In one embodiment, the functional effect is a physical effect or a chemical effect. In another embodiment, the polypeptide is expressed in a eukaryotic host cell or cell membrane. In another embodiment, the functional effect is determined by measuring ion flux, changes in ion concentrations, changes in current or changes in voltage. In another embodiment, the functional effect is determined by measuring ligand binding to the channel.

In one embodiment, the polypeptide is recombinant. In another embodiment, the cation channel is heteromeric. In another embodiment, the polypeptide is human CNG3B. In another embodiment, the polypeptide has an amino acid sequence of SEQ ID NO:1.

In another aspect, the present invention provides a method for identifying a compound that increases or decreases ion flux through a cyclic nucleotide-gated cation channel comprising a CNG3B polypeptide, the method comprising the steps of: (i) entering into a computer system an amino acid sequence of at least 25 amino acids of a CNG3B polypeptide or at least 75 nucleotides of a nucleic acid encoding the CNG3B polypeptide, the CNG3B polypeptide comprising a subsequence having at least 85% amino acid sequence identity to amino acids 210 to 661 of SEQ ID NO:1; (ii) generating a three-dimensional structure of the polypeptide encoded by the amino acid sequence; (iii) generating a three-dimensional structure of the cation channel comprising the CNG3B polypeptide; (iv) generating a three-dimensional structure of the compound; and (v) comparing the three-dimensional structures of the polypeptide and the compound to determine whether or not the compound binds to the polypeptide.

In another aspect, the present invention provides a method of modulating ion flux through a CNG cation channel comprising a CNG3B subunit to treat a disease in a subject, the method comprising the step of administering to the subject a therapeutically effective amount of a compound identified using the methods described herein.

In another aspect, the present invention provides a method of detecting the presence of CNG3B in human tissue, the method comprising the steps of: (i) isolating a biological sample; (ii) contacting the biological sample with an CNG3B-specific reagent that selectively associates with CNG3B; and, (iii) detecting the level of CNG3B-specific reagent that selectively associates with the sample.

In one embodiment, the hCNG3B5-specific reagent is selected from the group consisting of: CNG3B-specific antibodies, CNG3B-specific oligonucleotide primers, and CNG3B-nucleic acid probes.

In another aspect, the present invention provides, in a computer system, a method of screening for mutations of a human CNG3B gene, the method comprising the steps of: (i) entering into the computer a first nucleic acid sequence encoding a CNG3B polypeptide having a nucleotide sequence of, SEQ ID NO:2 or SEQ ID NO:3, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

In another aspect, the present invention provides, in a computer system, a method for identifying a three-dimensional structure of a CNG3B polypeptide, the method comprising the steps of: (i) entering into the computer system an amino acid sequence of at least 35 amino acids of the CNG3B polypeptide or at least 105 nucleotides of a nucleic acid encoding the polypeptide, the CNG3B polypeptide comprising a subsequence having at least 85% amino acid sequence identity to amino acids 221 to 661 of SEQ ID NO:1; and (ii) generating a three-dimensional structure of the polypeptide encoded by the amino acid sequence.

In one embodiment, the method further comprises the step of generating a three-dimensional structure of the cation channel comprising the CNG3B polypeptide.

In one embodiment, the amino acid sequence is a primary structure and wherein said generating step includes the steps of: (i) forming a secondary structure from said primary structure using energy terms determined by the primary structure; and (ii) forming a tertiary structure from said secondary structure using energy terms determined by said secondary structure. In another embodiment, the generating step further includes the step of forming a quaternary structure from said tertiary structure using anisotropic terms encoded by the tertiary structure. In another embodiment, the method further comprises the step of identifying regions of the three-dimensional structure of the polypeptide that bind to ligands and using the regions to identify ligands that bind to a cation channel comprising a CNG3B polypeptide.

BRIEF DESCRIPTION OF THE DRAWINGS

FIG. 1. Amino acid alignment of CNG3B (SEQ ID NO:13) with human CNGA1 (SEQ ID NO:14) and CNGA3 (SEQ ID NO:15). Identical residues are shaded and numbers at the left margin indicate amino acid position.

FIG. 2. Complete CNG3B sequence (SEQ ID NO:16) derived from assembly of PCR fragments.

FIG. 3. Complete CNG3B coding nucleotide sequence (SEQ ID NO:3).

FIG. 4. Complete CNG3B amino acid sequence (SEQ ID NO:1).

DETAILED DESCRIPTION OF THE INVENTION

I. Introduction

The present invention provides for the first time nucleic acids encoding CNG3B, a member of the CNG family of cyclic nucleotide gated cation channels. Members of this family are polypeptide subunits of cation channels having six transmembrane regions, a pore motif, and a cytoplasmic cyclic nucleotide binding domain. CNG3B is similar to members of this family that are beta subunits, and is thus most likely a beta subunit itself. As beta subunits require heteromultimerization to function, and as CNG3B is expressed in the retina, it is also likely that CNG3B forms functional heteromultimers with CNGA1 and/or CNGA3, two CNG alpha subunits that are expressed in the retina. Because CNG3B is expressed in the retina, modulators of CNG3B function can be identified which would be useful in the treatment of visual disorders. In addition, as CNG3B is expressed in the testes, and thus plays a role in sperm motility, and modulators of CNG3B would also be useful in the treatment of infertility or as contraceptives.

The invention therefore provides methods of screening for activators and inhibitors of cation channels that contain a CNG3B subunit. Such modulators of cation channel activity are useful for treating disorders, including visual disorders, as well as for the treatment of male infertility or as contraceptives.

Furthermore, the invention provides assays for CNG activity where CNG3B acts as a direct or indirect reporter molecule. Such uses of CNG3B as a reporter molecule in assay and detection systems have broad applications, e.g., CNG3B can be used as a reporter molecule to measure changes in cation concentration, membrane potential, current flow, ion flux, transcription, signal transduction, receptor-ligand interactions, second messenger concentrations, in vitro, in vivo, and ex vivo. In one embodiment, CNG3B can be used as an indicator of current flow in a particular direction (e.g., outward or inward cation flow), and in another embodiment, CNG3B can be used as an indirect reporter via attachment to a second reporter molecule such as green fluorescent protein.

The invention also provides for methods of detecting CNG3B nucleic acid and protein expression, allowing investigation of the channel diversity provided by CNG3B family members, as well as diagnosis of disorders, including visual disorders and male infertility.

Finally, the invention provides for a method of screening for mutations of CNG3B genes or proteins. The invention includes, but is not limited to, methods of screening for mutations in CNG3B with the use of a computer. Similarly, the invention provides for methods of identifying the three-dimensional structure of CNG3B polypeptides, as well as the resulting computer readable images or data that comprise the three dimensional structure of CNG3B polypeptides. Other methods for screening for mutations of CNG3B genes or proteins include high density oligonucleotide arrays, PCR, immunoassays and the like.

Functionally, CNG3B polypeptides are subunits, e.g., beta subunits, of cyclic nucleotide-gated cation channels. Typically, CNG3B-containing channels are heteromeric and contain, in addition to the CNG3B subunits, one or more CNG alpha subunits. The presence of CNG3B in a cation channel may modulate the activity of the heteromeric channel and thus enhance channel diversity. Channel diversity is also enhanced with alternatively spliced forms of CNG3B genes. CNG3B nucleic acids have been isolated from cDNAs from a plurality of human tissues, e.g., the retina and testes.

Structurally, the nucleotide sequence of human CNG3B (SEQ ID NOS:2–3) encodes a polypeptide monomer with a predicted molecular weight of approximately 92 kD and a predicted molecular weight range of 87–97 kD. In particular, the amino acid sequence of CNG3B has a conserved region corresponding to amino acids 210–661. This conserved region contains the characteristic motifs of cyclic nucleotide gated channels. These motifs include six predicted transmembrane domains, a region homologous to the pore motif of cyclic nucleotide-gated channels (Zagotta & Seigelbaum, *Ann. Rev. Neurosci.* 19:235–263 (1996); Sun et al., *Neuron* 16:141–149 (1996)) and a cyclic nucleotide binding motif. All proteins containing these three characteristic motifs have been shown to function as alpha or beta subunits of cyclic nucleotide-gated cation channels (Dhallan et al., *J. Neurosci.* 12:3248–3256 (1992); Wissinger et al., *Eur. J. Neurosci.* 9:2512–2521 (1997); Gerstner et al., *J. Neurosci.* 20:1324–1332 (2000); Liman & Buck, *Neuron* 13:611–621 (1994); Chen et al., *Nature* 362:764–767 (1993); and Dhallan et al., *Nature* 347:184–187 (1990)). Related CNG3B genes from other species share at least about 60%, 65%, 70%, 75%, 80%, preferably 85%, 90% or 95% amino acid identity in the conserved region.

The present invention also provides polymorphic variants of the human CNG3B depicted in SEQ ID NO:1: variant #1, in which a lysine residue is substituted for the arginine residue at amino acid position 142; variant #2, in which an asparagine residue is substituted for the aspartic acid residue at amino acid position 154; variant #3, in which a valine residue is substituted for the leucine residue at amino acid position 675; and variant #4, in which a serine residue is substituted for the glycine residue at amino acid position 682.

Specific regions of CNG3B nucleotide and amino acid sequence may be used to identify CNG3B polymorphic variants, interspecies homologs, and alleles. This identification can be made in vitro, e.g., under stringent hybridization conditions and sequencing, or by using the sequence information in a computer system for comparison with other nucleotide sequences, or using antibodies raised against CNG3B. Typically, identification of CNG3B polymorphic variants, orthologs, and alleles is made by comparing the amino acid sequence (or the nucleic acid encoding the amino acid sequence) of a conserved region corresponding to amino acids 210–661 of SEQ ID NO:1. Amino acid identity of approximately at least 60% or above, 70%, 65%, 75%, 80%, preferably 85%, most preferably 90–95% or above in the conserved region (amino acids 210–661 of SEQ ID NO:1) typically demonstrates that a protein is a CNG3B polymorphic variant, interspecies homolog, or allele. Sequence comparison is typically performed using the BLAST or BLAST 2.0 algorithm with default parameters, discussed below.

CNG3B polymorphic variants, interspecies homologs, and alleles can be confirmed by expressing or co-expressing the putative CNG3B polypeptide monomer and examining whether it forms a cation channel with CNG family functional and biochemical characteristics. This assay is used to demonstrate that a protein having about 60% or greater, 65%, 70%, 75%, 80%, preferably 85%, 90%, or 95% or greater amino acid identity to the conserved region of CNG3B shares the same functional characteristics as CNG3B and is therefore a species of CNG3B. Typically, human CNG3B having the amino acid sequence of SEQ ID NO:1 is used as a positive control in comparison to the putative CNG3B protein to demonstrate the identification of a CNG3B polymorphic variant, ortholog, conservatively-modified variant, mutant, or allele.

CNG3B nucleotide and amino acid sequence information may also be used to construct models of cyclic nucleotide-gated cation channels in a computer system. These models are subsequently used to identify compounds that can activate or inhibit cyclic nucleotide-gated cation channels comprising CNG3B polypeptides. Such compounds that modulate the activity of channels comprising CNG3B polypeptides can be used to investigate the role of CNG3B polypeptides in the modulation of channel activity and in channel diversity.

The isolation of biologically active CNG3B for the first time provides a means for assaying for inhibitors and activators of cyclic nucleotide-gated cation channels that comprise CNG3B subunits. Biologically active CNG3B polypeptides is useful for testing inhibitors and activators of cyclic nucleotide-gated cation channels comprising subunits of CNG3B, using in vivo and in vitro expression that measure, e.g., changes in voltage or current. Such activators and inhibitors identified using a cation channel comprising at least one CNG3B subunit, optionally up to four CNG3B subunits, can be used to further study cyclic nucleotide-gating, channel kinetics and conductance properties of cation channels. Such activators and inhibitors are useful as pharmaceutical agents for treating diseases involving abnormal ion flux, e.g., disorders, including visual disorders and male infertility, as described above. Methods of detecting CNG3B nucleic acids and polypeptides and expression of channels comprising CNG3B polypeptides are also useful for diagnostic applications for diseases involving abnormal ion flux, e.g., as described above. For example, chromosome localization of the gene encoding human CNG3B can be used to identify diseases caused by and associated with CNG3B. Methods of detecting CNG3B are also useful for examining the role of CNG3B in channel diversity and modulation of channel activity.

II. Definitions

As used herein, the following terms have the meanings ascribed to them unless specified otherwise.

The phrase "conserved region" refers to the region of CNG3B that structurally identifies this particular protein (approximately amino acids 210–661 of SEQ ID NO:1). This region can be used to identify CNG3B polymorphic variants, orthologs, conservatively modified variants, mutants, homologs, and alleles, each of which will typically comprise at least about 60%, 65%, 70%, 75%, 80%, preferably 85%, 90%, 95%, or greater amino acid sequence identity to the conserved region or the full length CNG3B sequence, through amino acid sequence identity comparison using a sequence comparison algorithm such as BLASTP, using the parameters described herein.

"CNG3B" refers to a polypeptide that is a subunit or monomer of a cyclic nucleotide gated cation channel, and a member of the CNG family. When CNG3B is part of a cation channel, e.g., a heteromeric cation channel, the channel has the characteristic of cyclic nucleotide gating. The term CNG3B therefore refers to CNG3B polymorphic variants, alleles, mutants, and interspecies homologs that: (1) have a subsequence that has greater than about 60% amino acid sequence identity, 65%, 70%, 75%, 80%, preferably 85%, 90%, or 95% amino acid sequence identity, to the CNG3B conserved region (amino acids 210–661 of SEQ ID NO:1), or, optimally, comprise 60%, 65%, 70%, 75%, 80%, 85%, 90%, 95%, or greater identity to a CNG3B amino acid sequence of SEQ ID NO:1; (2) bind to antibodies, e.g., polyclonal antibodies, raised against an immunogen comprising an amino acid sequence of SEQ ID NO: 1 or amino acids 210–661 of SEQ ID NO:1, and conservatively modified variants thereof; (3) specifically hybridize under stringent hybridization conditions to a sequence of SEQ ID NOS:2–3 or a nucleotide sequence encoding amino acids 210–661 of SEQ ID NO:1, and conservatively modified variants thereof; or (4) are amplified by primers that specifically hybridize under stringent hybridization conditions to the same sequence as a primer set selected from the group consisting of SEQ ID NOS:4–12.

The phrase "cyclic nucleotide-gated" activity or "cyclic nucleotide-gating" refers to a characteristic of a cation channel composed of individual polypeptide monomers or subunits. Generally, cyclic-nucleotide-gated cation channels are a class of non-selective cation channels that are opened by direct binding of cyclic nucleotides such as cGMP and cAMP. CNG channels are highly permeable to $Na^+$ and $Ca^{2+}$, and their activation leads to depolarization and increases in internal $Ca^{2+}$ concentrations. CNG channels can thus link changes in cytoplasmic cyclic nucleotide levels to changes in cellular excitability, secretion of neurotransmitters, and/or stimulation of calcium-dependent pathways. CNG channels play an important role in sensory signal transduction in numerous cells, e.g., retinal, olfactory, or taste bud cells, in response to primary sensory stimuli such as light and aerosolized or dissolved molecules. In photoreceptor cells, CNG channels are open in darkness due to a high basal concentration of cGMP, causing a tonic depolarization of the membrane and constitutive neurotransmitter release. Upon stimulation by light, cGMP levels drop, closing the CNG channels, and in turn causing a hyperpolarization of the membrane, a drop in the internal $Ca^{2+}$ concentration, and a decrease in neurotransmitter release. CNG channels may also interact with second messenger systems such as the Nitric Oxide pathway. CNG channels also play a role in other tissues, such as the testes, where they may be involved in the chemotaxis of sperm by regulating internal $Ca^{2+}$ concentrations (see, e.g., Weyand, I., et al., *Nature*, 368:859–863, 1994).

"Homomeric channel" refers to a CNG channel composed of identical alpha subunits, whereas "heteromeric channel" refers to a CNG channel composed of at least one CNG alpha subunit, e.g., CNGA1 or CNGA3, plus at least one other type of alpha or beta subunit, e.g., CNG3B.

A "beta subunit" is a polypeptide monomer that is an auxiliary subunit of a CNG cation channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "functional effects" in the context of assays for testing compounds affecting a channel comprising CNG3B includes the determination of any parameter that is indirectly or directly under the influence of the channel. It includes physical and chemical effects, e.g., changes in ion flux and membrane potential, changes in ligand binding, and also includes other physiologic effects such as increases or decreases of transcription or hormone release.

"Determining the functional effect" refers to examining the effect of a compound that increases or decreases ion flux on a cell or cell membrane in terms of cell and cell membrane function. The ion flux can be any ion that passes through a channel and analogues thereof, e.g., sodium, calcium. Preferably, the term refers to the functional effect of the compound on the channels comprising CNG3B, e.g., changes in ion flux including radioisotopes, current amplitude, membrane potential, current flow, transcription, protein binding, phosphorylation, dephosphorylation, second messenger concentrations (cAMP, cGMP, $Ca^{2+}$, $IP_3$), ligand binding, changes in ion concentration, and other physiological effects such as hormone and neurotransmitter release, as well as changes in voltage and current. Such functional effects can be measured by any means known to those skilled in the art, e.g., patch clamping, voltage-sensitive dyes, ion sensitive dyes, whole cell currents, radioisotope efflux, inducible markers, and the like.

"Inhibitors," "activators" or "modulators" of cyclic nucleotide-gated cation channels comprising a CNG3B polypeptide refer to inhibitory or activating molecules identified using in vitro and in vivo assays for CNG3B channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing a CNG3B polypeptide, e.g., CNG3B, in cells or cell membranes and then measuring flux of ions through the channel and determining changes in polarization (i.e., electrical potential). Alternatively, cells expressing endogenous CNG3B channels can be used in such assays. To examine the extent of inhibition, samples or assays comprising a CNG3B channel are treated with a potential activator or inhibitor and are compared to control samples without the inhibitor. Control samples (untreated with inhibitors) are assigned a relative CNG3B activity value of 100%. Inhibition of channels comprising CNG3B is achieved when the CNG3B activity value relative to the control is about 90%, preferably 50%, more preferably 25–0%. Activation of channels comprising CNG3B is achieved when the CNG3B activity value relative to the control is 110%, more preferably 150%, most preferably at least 200–500% higher or 1000% or higher.

"Biologically active" CNG3B polypeptides refers to CNG3B polypeptides, e.g., CNG3B, that have the ability to form a cation channel having the characteristic of cyclic nucleotide-gating tested as described herein.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated CNG3B nucleic acid is separated from open reading frames that flank the CNG3B gene and encode proteins other than CNG3B. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by readthrough transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 15 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptide of SEQ ID NO:1 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, 65%, 70%, 75%, 80%, preferably 85%, 90%, or 95% identity over a specified sequence such as SEQ ID NO:1 or such as amino acids 210–661 of SEQ ID NO:1), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to CNG3B nucleic acids and proteins, e.g., CNG3B, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Fundamental Immunology (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990))

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552–554 (1990); Marks et al., *Biotechnology* 10:779–783 (1992)).

An "anti-CNG3B" antibody is an antibody or antibody fragment that specifically binds a polypeptide encoded by a CNG3B gene, cDNA, or a subsequence thereof, e.g., CNG3B.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to CNG3B, as shown in SEQ ID NO:1, or splice variants, or portions thereof, can be selected to obtain only those polyclonal antibodies that are specifically immunoreactive with CNG3B and not with other proteins. This selection may be achieved by subtracting out antibodies that cross-react with molecules such as other CNG family members. In addition, polyclonal antibodies raised to CNG3B polymorphic variants, alleles, orthologs, and conservatively modified variants can be selected to obtain only those antibodies that recognize CNG3B, but not other CNG family members. In addition, antibodies to human CNG3B but not other CNG3B orthologs can be selected in the same manner. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, *A Laboratory Manual* (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains CNG3B polypeptides or nucleic acid encoding a CNG3B protein. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. Isolating a Gene Encoding a CNG3B Polypeptide

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984). Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding CNG3B Polypeptides In general, the nucleic acid sequences encoding CNG3B and related nucleic acid sequence homologs are cloned from cDNA and genomic DNA libraries or isolated using amplification techniques with oligonucleotide primers. For example, CNG3B sequences are typically isolated from human nucleic acid (genomic or cDNA) libraries by hybridizing with a nucleic acid probe or polynucleotide, the sequence of which can be derived from SEQ ID NOS:2–3, preferably from the region encoding the conserved region (see, e.g., amino acids 210 to 661 of SEQ ID NO:1). A suitable tissue from which CNG3B RNA and cDNA can be isolated is retina or testes. Preferably, the template for the amplification is first strand cDNA made from some part of the human retina.

Amplification techniques using primers can also be used to amplify and isolate CNG3B from DNA or RNA. The following primers can also be used to amplify a sequence of human CNG3B:

| | |
|---|---|
| TCTATCTCCTGTGGCTCTTGCTTGTC | (SEQ ID NO: 4) |
| GAGTCTGGGCTGGATAAATAGCATATC | (SEQ ID NO: 5) |
| AGGAATTGGCACTACTAGATGGGTG | (SEQ ID NO: 6) |
| TTCATGAGGATCCTTTCAGAATCTGG | (SEQ ID NO: 7) |
| GGAAACCGTCGAACTGCCAATGTGGT | (SEQ ID NO: 8) |
| CGGGTTTGCCAATCTTTTAACTCTAGAC | (SEQ ID NO: 9) |
| GTCCGCAATAAGCCAGTAGTGTATG | (SEQ ID NO: 10) |
| TGACAAGCTTCCGCCATGTTTAAATCGCTGACAA AAGTC and | (SEQ ID NO: 11) |
| TGACGAATTCTCCCAGCATGTCGTTTCCCCTCGT TAA. | (SEQ ID NO: 12). |

These primers can be used, e.g., to amplify either the full length sequence or a probe of one to several hundred nucleotides, which is then used to screen a library for full-length CNG3B. For example, Oligo 1 (SEQ ID NO:4) can be used with Oligo 2 (SEQ ID NO:5) to produce a 180 bp band, and Oligo 3 (SEQ ID NO:6) and Oligo 4 (SEQ ID NO:7) can produce a 787 bp band. Oligos 8 (SEQ ID NO:11) and Oligo 9 (SEQ ID NO:12) can be used to amplify the entire coding region. Further, in conjunction with other oligos, Oligo 8 can be used with Oligos 2, 4, or 7 (SEQ ID NO:10) to produce bands of approximately 195 bp, 1.25 kb, or 145 bp, respectively. Similarly, Oligo 9 can be used with Oligos 1, 3, 5 (SEQ ID NO:8), or 6 (SEQ ID NO:9) to produce fragments of approximately 1.89 kb, 1.40 kb, 735 bp, or 703 bp, respectively.

Nucleic acids encoding CNG3B and other CNG3B family members can also be isolated from expression libraries using antibodies as probes. Such polyclonal or monoclonal antibodies can be raised using the sequence of SEQ ID NO:1, or an immunogenic portion thereof, e.g., amino acids 210 to 661 of SEQ ID NO:1.

CNG3B polymorphic variants, orthologs, and alleles that are substantially identical to the conserved region of CNG3B can be isolated using CNG3B nucleic acid probes and oligonucleotides under stringent hybridization conditions, by screening libraries. Alternatively, expression libraries can be used to clone CNG3B and CNG3B polymorphic variants, orthologs, and alleles by detecting expressed homologs immunologically with antisera or purified antibodies made against human CNG3B or portions thereof (e.g., the conserved region of human CNG3B), which also recognize and selectively bind to the CNG3B homolog.

To make a cDNA library, one should choose a source that is rich in CNG3B mRNA, e.g., human CNG3B mRNA, e.g., retina or testes. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating CNG3B and CNG3B nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human CNG3B directly from mRNA, from cDNA, from genomic libraries or cDNA libraries. Degenerate oligonucleotides can be designed to amplify CNG3B homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of CNG3B encoding mRNA in physiological samples, for nucleic acid sequencing, or for other purposes. Genes amplified by the PCR reaction can be purified from agarose gels and cloned into an appropriate vector.

Gene expression of CNG3B can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology and the like.

Synthetic oligonucleotides can be used to construct recombinant CNG3B genes for use as probes or for expression of protein. This method is performed using a series of overlapping oligonucleotides usually 40–120 bp in length, representing both the sense and non-sense (antisense) strands of the gene. These DNA fragments are then annealed, ligated and cloned. Alternatively, amplification techniques can be used with precise primers to amplify a specific subsequence of the CNG3B gene. The specific subsequence is then ligated into an expression vector.

The gene for CNG3B is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding CNG3B, one typically subclones the gene into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the CNG3B protein are available in, e.g., *E. coli, Bacillus sp.,* and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the CNG3B encoding nucleic acid in host cells. A typical expression cassette thus contains a promoter operably linked to the nucleic acid sequence encoding CNG3B and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a CNG3B encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical—any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of CNG3B protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing CNG3B.

After the expression vector is introduced into the cells, the transfected cells are cultured under conditions favoring expression of CNG3B, which is recovered from the culture using standard techniques identified below.

IV. Purification of CNG3B Polypeptides

Either naturally occurring or recombinant CNG3B can be purified for use in functional assays. Naturally occurring CNG3B monomers can be purified, e.g., from human tissue such as retina or testes or any other source of a CNG3B homolog. Recombinant CNG3B monomers can be purified from any suitable expression system.

The CNG3B monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant CNG3B monomers are being purified. For example, proteins having established molecular adhesion properties can be reversibly fused to the CNG3B monomers. With the appropriate ligand, the CNG3B monomers can be selectively adsorbed to a purification column and then freed from the column in a relatively pure form. The fused protein is then removed by enzymatic activity. Finally the CNG3B monomers could be purified using immunoaffinity columns.

A. Purification of CNG3B Monomers from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the CNG3B monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human CNG monomers are separated from other bacterial proteins by standard separation techniques, e.g., with Ni-NTA agarose resin.

Alternatively, it is possible to purify the CNG3B monomers from bacteria periplasm. After lysis of the bacteria, when the CNG3B monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying CNG3B Monomers

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the CNG3B monomers (e.g., approximately 92 kD) can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The CNG3B monomers can also be separated from other proteins on the basis of size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of CNG3B Polypeptides

In addition to the detection of CNG3B genes and gene expression using nucleic acid hybridization technology, one can also use immunoassays to detect the CNG3B monomers of the invention. Immunoassays can be used to qualitatively or quantitatively analyze the CNG3B monomers. A general overview of the applicable technology can be found in Harlow & Lane, *Antibodies: A Laboratory Manual* (1988).

A. Antibodies to CNG3B Monomers

Methods of producing polyclonal and monoclonal antibodies that react specifically with CNG3B monomers, or CNG3B monomers from particular species such as human CNG3B, are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of CNG3B monomers may be used to produce antibodies specifically reactive with CNG3B monomers. For example, recombinant CNG3B monomers or an antigenic fragment thereof, such as the conserved region (see, e.g., amino acids 210–661 of SEQ ID NO:1), can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-CNG family proteins and other CNG family proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular CNG3B ortholog, such as human CNG3B, can also be made, by subtracting out other cross-reacting orthologs from a species such as a non-human mammal.

Once the specific antibodies against a CNG3B are available, the CNG3B can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

The CNG3B polypeptides of the invention can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the CNG3B or an antigenic subsequence thereof). The antibody (e.g., anti-CNG3B) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled CNG3B polypeptide or a labeled anti-CNG3B antibody. Alternatively, the labeling agent may be a third moiety, such a secondary antibody, which specifically binds to the antibody/CNG3B complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting the CNG3B in samples may be either competitive or noncompetitive. Noncompetitive immunoassays are assays in which the amount of antigen is directly measured. In one preferred "sandwich" assay, for example, the anti-CNG3B subunit antibodies can be bound directly to a solid substrate on which they are immobilized. These immobilized antibodies then capture CNG3B present in the test sample. The CNG3B monomers are thus immobilized and then bound by a labeling agent, such as a second CNG3B antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the CNG3B present in the sample is measured indirectly by measuring the amount of known, added (exogenous) CNG3B displaced (competed away) from an anti-CNG3B antibody by the unknown CNG3B present in a sample. In one competitive assay, a known amount of the CNG3B is added to a sample and the sample is then contacted with an antibody that specifically binds to the CNG3B. The amount of exogenous CNG3B bound to the antibody is inversely proportional to the concentration of the CNG3B present in the sample. In a particularly preferred embodiment, the antibody is immobilized on a solid substrate. The amount of CNG3B bound to the antibody may be determined either by measuring the amount of CNG3B present in a CNG3B/antibody complex, or alternatively by measuring the amount of remaining uncomplexed protein. The amount of CNG3B may be detected by providing a labeled CNG3B molecule.

A hapten inhibition assay is another preferred competitive assay. In this assay the known CNG3B is immobilized on a solid substrate. A known amount of anti-CNG3B antibody is added to the sample, and the sample is then contacted with the immobilized CNG3B. The amount of anti-CNG3B antibody bound to the known immobilized CNG3B is inversely proportional to the amount of CNG3B present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations for CNG3B. For example, a CNG3B protein at least partially corresponding to an amino acid sequence of SEQ ID NO:1 or an immunogenic region thereof, such as the conserved region (e.g., amino acids 210–661 of SEQ ID NO:1), can be immobilized to a solid support. Other proteins such as other CNG family members are added to the assay so as to compete for binding of the antisera to the immobilized antigen. The ability of the added proteins to compete for binding of the antisera to the immobilized protein is compared to the ability of the CNG3B or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. Antibodies that specifically bind only to particular orthologs of CNG3B, such as human CNG3B, can also be made using this methodology.

The immunoabsorbed and pooled antisera are then used in a competitive binding immunoassay as described above to compare a second protein, thought to be perhaps an allele, ortholog, or polymorphic variant of CNG3B, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by CNG3B that is required to inhibit 50% of binding, then the second protein is said to specifically bind to the polyclonal antibodies generated to the respective CNG3B immunogen.

Other Assay Formats

Western blot (immunoblot) analysis is used to detect and quantify the presence of the CNG3B in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind CNG3B. The anti-CNG3B antibodies specifically bind to CNG3B on the solid support. These antibodies may be directly labeled or alternatively may be subsequently detected using labeled antibodies (e.g., labeled sheep anti-mouse antibodies) that specifically bind to the anti-CNG3B antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize CNG3B, or secondary antibodies that recognize anti-CNG3B antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of CNG3B

A. Assays

Human CNG3B and CNG3B alleles, orthologs, and polymorphic variants are subunits of cation channels. The activity of a cation channel comprising CNG3B can be assessed using a variety of in vitro and in vivo assays, e.g. measuring current, measuring membrane potential, measuring ion flux, e.g., cations such as sodium or calcium, measuring ion concentration, measuring second messengers and transcription levels, measuring ligand binding, and using, e.g., voltage-sensitive dyes, ion sensitive dyes such as cation (e.g., sodium or calcium) sensitive dyes, radioactive tracers, and patch-clamp electrophysiology.

In preferred embodiments, the activity of a CNG cation channel will be detected by detecting cation, e.g., calcium or sodium, concentration or flux using an ion (e.g., calcium or sodium) specific dye, e.g., a fluorescent dye. Any such dye, a large number of which are well known to those of skill in the art, can be used. For example, any of a number of fluorescent probes that show a spectral response upon binding $Ca^{2+}$ allowing the detection of changes in intracellular free $Ca^{2+}$ concentrations using fluorescence microscopy, flow cytometry or fluorescence spectroscopy, can be used.

Furthermore, such assays can be used to test for inhibitors and activators of channels comprising CNG3B. Such modulators of a cation channel are useful for treating various disorders involving cation channels, e.g., vision disorders or male infertility. Such modulators are also useful as contraceptives. Such modulators are also useful for investigation of the channel diversity provided by CNG family members and the regulation/modulation of cation channel activity provided by CNG family members such as CNG3B.

Modulators of the CNG cation channels are tested using biologically active CNG3B, either recombinant or naturally occurring, preferably human CNG3B. CNG3B can be isolated, co-expressed or expressed in a cell, or expressed in a membrane derived from a cell. In such assays, CNG3B is typically expressed in combination with other CNG proteins, including at least one alpha subunit (e.g., CNGA1 or CNGA3), to form a heteromeric cation channel. CNG3B polypeptides can also be expressed with additional beta subunits. Modulation is tested using one of the in vitro or in vivo assays described above. Samples or assays that are treated with a potential cation channel inhibitor or activator are compared to control samples without the test compound, to examine the extent of modulation. Often, such assays are performed in the presence of a cyclic nucleotide, e.g., cAMP or cGMP, and the ability of the test agent to modulate the effect of the cyclic nucleotide on the channel is detected. Control samples (untreated with activators or inhibitors) are assigned a relative cation channel activity value of 100. Inhibition of channels comprising a CNG3B polypeptide is achieved when the cation channel activity value relative to the control is about 90%, preferably 50%, more preferably 25%. Activation of channels comprising a CNG3B polypeptide is achieved when the cation channel activity value relative to the control is 110%, more preferably 150%, more preferable 200% higher. Compounds that increase the flux of ions will cause a detectable increase in the ion current density by increasing the probability of a channel comprising a CNG3B polypeptide being open, by decreasing the probability of it being closed, by increasing conductance through the channel, and/or by allowing the passage of ions.

Changes in ion flux may be assessed by determining changes in polarization (i.e., electrical potential) of the cell or membrane expressing the cation channel comprising a CNG3B polypeptide. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et at., New Engl. J. Med. 336: 1575–1595 (1997)). Whole cell currents are conveniently determined using the standard methodology (see, e.g., Hamil et at., PFlugers. Archiv. 391:85 (1981). Other known assays include fluorescence assays using ion sensitive dyes (see, e.g., Vestergarrd-Bogind et al., J. Membrane Bid. 88:67–75 (1988); Daniel et at., J. Pharmacol. Meth. 25:185–193 (1991); Holevinsky et at., J. Membrane Biology 137:59–70 (1994)). Examples of such dyes useful for the detection of calcium include, but are not limited to, fura-2, bis-fura 2, indo-1, Quin-2, Quin-2 AM, Benzothiaza-1, Benzothiaza-2, indo-5F, Fura-FF, BTC, Mag-Fura-2, Mag-Fura-5, Mag-Indo-1, fluo-3, rhod-2, fura-4F, fura-5F, fura-6F, fluo-4, fluo-5F, fluo-5N, Oregon Green 488 BAPTA, Calcium Green, Calcein, Fura-C 18, Calcium Green-C 18, Calcium Orange, Calcium Crimson, Calcium Green-5N, Magnesium Green, Oregon Green 488 BAPTA-1, Oregon Green 488 BAPTA-2, X-rhod-1, Fura Red, Rhod-5F, Rhod-5N, X-Rhod-5N, Mag-Rhod-2, Mag-X-Rhod-1, Fluo-5N, Fluo- 5F, Fluo-4FF, Mag-Fluo-4, Aequorin, dextran conjugates or any other derivatives of any of these dyes, and others (see, e.g., the catalog or Internet site for Molecular Probes, Eugene, Oreg.; see, also, Nuccitelli, ed., *Methods in Cell Biology, Volume* 40: *A Practical Guide to the Study of Calcium in Living Cells*, Academic Press (1994); Lambert, ed., *Calcium Signaling Protocols* (Methods in Molecular Biology Volume 114), Humana Press (1999); W. T. Mason, ed., *Fluorescent and Luminescent Probes for Biological Activity. A Practical Guide to Technology for Quantitative Real-Time Analysis*, Second Ed, Academic Press (1999)). Examples of sodium indicators include, but are not limited to, SBFI, and Sodium Green (see, e.g., Molecular probes catalog or Internet site; Mason, supra).

Assays for compounds capable of inhibiting or increasing cation flux through the channel proteins comprising a CNG3B polypeptide can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 µM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as sodium or calcium ions. The ions can be measured in a variety of standard ways. They can be measured directly by concentration changes of the ions, e.g., changes in intracellular concentrations, e.g., using any of the dyes listed supra, or radiolabeled ions, or indirectly by membrane potential. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), intracellular calcium changes, hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as cyclic nucleotides.

Preferably, the CNG3B polypeptide that is a part of the cation channel used in the assay will have the sequence displayed in SEQ ID NO:1 or a conservatively modified variant thereof. Alternatively, the CNG3B of the assay will be derived from a eukaryote and include an amino acid subsequence having substantial amino acid sequence identity to the conserved region (see, e.g., amino acids 210 to 661 of SEQ ID NO:1) of human CNG3B. Generally, the amino acid sequence identity will be at least 60%, 65%, 70%, 75%, 80%, preferably 85%, or 90%, most preferably at least 95%.

CNG3B orthologs, alleles, polymorphic variants, and conservatively modified variants will generally confer substantially similar properties on a channel comprising a CNG3B polypeptide, as described above. In a preferred embodiment, the cell placed in contact with a compound that is suspected to be a CNG3B homolog is assayed for increasing or decreasing ion flux in a eukaryotic cell, e.g., an oocyte of *Xenopus* (e.g., *Xenopus laevis*) or a mammalian cell such as a CHO or HeLa cell. Channels that are affected by compounds in ways similar to CNG3B are considered homologs or orthologs of CNG3B.

B. Modulators

The compounds tested as modulators of CNG channels comprising a CNG3B subunit can be any small chemical compound, or a biological entity, such as a protein, sugar, nucleic acid or lipid. Alternatively, modulators can be genetically altered versions of a CNG3B subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a CNG channel comprising a human CNG3B subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100–about 1500 different compounds. It is possible to assay many plates per day; assay screens for up to about 6,000, 20,000, 50,000, or 100,000 or more different compounds are possible using the integrated systems of the invention.

C. Solid State and Soluble High throughput Assays

In one embodiment the invention provides soluble assays using cation channels comprising a CNG3B polypeptide, a membrane comprising a CNG3B cation channel, or a cell or tissue expressing cation channels comprising a CNG3B polypeptide, either naturally occurring or recombinant. In another embodiment, the invention provides solid phase based in vitro assays in a high throughput format, where a CNG3B cation channel is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100–about 1500 different compounds. It is possible to assay many plates per day; assay screens for up to about 6,000, 20,000, 50,000, or more than 100,000 different compounds are possible using the integrated systems of the invention.

The channel of interest, or a cell or membrane comprising the channel of interest, can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993)). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

VII. Computer Assisted Drug Design using CNG3B

Yet another assay for compounds that modulate the activities of a CNG3B channel involves computer assisted drug design, in which a computer system is used to generate a three-dimensional structure of CNG3B based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other cation channel subunits. These regions are then used to identify ligands that bind to the protein or region where CNG3B interacts with other cation channel subunits.

The three-dimensional structural model of the protein is generated by entering channel protein amino acid sequences of at least 25, 50, 75 or 100 amino acid residues or corresponding nucleic acid sequences encoding a CNG3B monomer into the computer system. The amino acid sequence of each of the monomers is selected from the group consisting of SEQ ID NO:1, conservatively modified versions thereof, and immunogenic portions thereof, e.g., comprising amino acids 210–661 of SEQ ID NO:1. The amino acid sequence represents the primary sequence or subsequence of each of the proteins, which encodes the structural information of the protein. At least 25, 50, 75, or 100 residues of the amino acid sequence (or a nucleotide sequence encoding at least about 25, 50, 75 or 100 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric cation channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the CNG3B protein to identify ligands that bind to CNG3B. Binding affinity between the protein and ligands is determined using energy terms to determine which ligands have an enhanced probability of binding to the protein.

Computer systems are also used to screen for mutations, polymorphic variants, alleles and interspecies homologs of CNG3B genes. Such mutations can be associated with disease states. Once the variants are identified, diagnostic assays can be used to identify patients having such mutated genes associated with disease states. Identification of the mutated CNG3B genes involves receiving input of a first nucleic acid, e.g., SEQ ID NOS:2–3, or an amino acid sequence encoding CNG3B, e.g., SEQ ID NO:1, and conservatively modified versions thereof, or an amino acid sequence comprising amino acids 210–661 of SEQ ID NO:1. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in CNG3B genes, preferably CNG3B genes, more preferably human CNG3B genes and mutations associated with disease states. The first and second sequences described above can be saved on a computer readable substrate.

Nucleic acids encoding CNG3B monomers can be used with high density oligonucleotide array technology (e.g., GeneChip™) to identify CNG3B homologs, orthologs, alleles, conservatively modified variants, and polymorphic variants in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

VIII. Cellular Transfection and Gene Therapy

The present invention provides the nucleic acids of CNG3B genes for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for CNG3B, under the control of a promoter, then expresses a CNG3B monomer of the present invention, thereby mitigating the effects of absent, partial inactivation, or abnormal expression of the CNG3B gene. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357: 455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Delivery of the gene or genetic material into the cell is the first step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.* 5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251–3260 (1985); Tratschin et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048–305 (1995); Kohn et al., *Nat. Med.* 1:1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors (Ellem et al., *Immunol Immunother.* 44(1):10–20 (1997); Dranoff et al., Hum. Gene Ther. 1:111–2 (1997)).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., *Lancet* 351:9117 1702–3 (1998), Kearns et al., *Gene Ther.* 9:748–55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 241: 5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topf et al., *Gene Ther.* 5:507–513 (1998); Sterman et al., *Hum. Gene Ther.* 7:1083–1089 (1998).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the CNG channels comprising a CNG3B subunit, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

X. Kits

Human CNG3B and its homologs are useful tools for examining expression and regulation of cation channels. Human CNG3B-specific reagents that specifically hybridize to CNG3B nucleic acid, such as CNG3B probes and primers, and CNG3B-specific reagents that specifically bind to the CNG3B protein, e.g., CNG3B antibodies, are used to examine expression and regulation.

Nucleic acid assays for the presence of CNG3B DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hames et al., eds. 1987). In addition, CNG3B protein can be detected with the various immunoassay techniques described above. The test sample is typically compared to both a positive control (e.g., a sample expressing recombinant CNG3B monomers) and a negative control.

The present invention also provides for kits for screening modulators of the cation channels of the invention. Such kits can be prepared from readily available materials and reagents. For example, such kits can comprise any one or more of the following materials: CNG3B monomers, reaction tubes, and instructions for testing the activities of cation channels containing CNG3B. A wide variety of kits and components can be prepared according to the present invention, depending upon the intended user of the kit and the particular needs of the user. For example, the kit can be tailored for in vitro or in vivo assays for measuring the activity of a cation channel comprising a CNG3B monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example I

Identification of Human CNG3B

Fragments of CNG3B were identified from a public genomic database in multiple exons from genomic BAC (Accession No. AC013751). As the 5' and 3' ends were not identifiable from the database, oligonucleotides were designed to clone a full-length CNG3B cDNA based on the AC013751 sequence.

An approximately 180 bp band from the middle of CNG3B was amplified from human cDNAs prepared from the retina, demonstrating expression in this tissue. The oligos used to amplify this band were 5'-(1) TCTATCTCCTGTGGCTCTTGCTTGTC (SEQ ID NO:4) (sense) and 5'-(2) GAGTCTGGGCTGGATAAATAGCATATC (SEQ ID NO:5) (antisense). An approximately 787 bp band from the middle of CNG3B was amplified from human retina using 5'-(3) AGGAATTGGCACTACTAGATGGGTG (SEQ ID NO:6) (sense) and 5'-(4) TTCATGAGGATCCTTTCA- GAATCTGG (SEQ ID NO:7) (antisense) oligos. An approximately 1.26 kb band from the middle of CNG3B was amplified from human retina using 5'-(1) TCTATCTCCT-GTGGCTCTTGCTTGTC (SEQ ID NO:4) (sense) and 5'-(4) TTCATGAGGATCCTTTCAGAATCTGG (SEQ ID NO:7) (antisense) oligos. The 1.26 kb fragment (5'-1 & 4) was subcloned and its sequence confirmed.

The complete 3' end of CNG3B was amplified by standard 3' RACE PCR techniques from human retina cDNA in two successive rounds. In the first round the gene specific primer used was 5'- (5) GGAAACCGTCGAACTGCCAAT-GTGGT (SEQ ID NO:8) (sense). This reaction was reamplified with a nested gene specific oligo 5'-(6) CGGGTTTGCCAATCTTTTAACTCTAGAC (SEQ ID NO:9) (sense) which produced a band approximately 810 bp in length that, when sequenced, was found to include the complete 3end of the CNG3B mRNA. This fragment overlapped with the original 1.26 kb CNG3B fragment to provide contiguous sequence. The 5' end of CNG3B was amplified from human retina cDNA using two rounds of standard 5' RACE PCR. The oligo 5'-(2) GAGTCTGGGCTGGATAAATAGCATATC (SEQ ID NO:5) (antisense) was used in the first round of RACE PCR and reamplified using the nested gene specific oligo 5'-(7) GTCCGCAATAAGCCAGTAGTGTATG (SEQ ID NO:10) (antisense). An approximately 830 bp fragment containing the complete 5' end of CNG3B including the start codon (Methionine) was isolated. This fragment also overlapped the original 1.26 kb fragment allowing us to determine the entire contiguous coding region of the CNG3B mRNA using both the 5' & 3' RACE products with the original 1.26 kb sequence.

The entire coding region of CNG3B was then isolated in a single fragment using oligonucleotides overlapping the CNG3B coding sequence ends as determined from sequence analysis of the above fragments. The oligonucleotides used were 5'-(8) TGACAAGCTTCCGCCATGTT-TAAATCGCTGACAAAAGTC (SEQ ID NO:11) (sense) and 5'-(9) TGACGAATTCTCCCAGCATGTCGTTTC-CCCTCGTTAA (SEQ ID NO:12) (antisense). The first oligonucleotide includes the initiator methionine, the first 24 coding nucleotides of the CNG3B gene, and, upstream, a HindIII restriction enzyme site for subcloning into plasmid vectors and a Kozak consensus sequence to boost translation. All nucleotides corresponding to CNG3B are in bold type. The second oligonucleotide is from the 3' untranslated sequence of CNG3B and includes an EcoRI restriction enzyme site for subcloning. Again, all nucleotides in bold correspond to the untranslated region of the 3' end of CNG3B (i.e., the only nucleotides required for the amplification of CNG3B are those in bold type from the two oligos above). The amplification conditions used were as follows: 24 cycles of 95° C. for 15 seconds, 70–58° C. for 15 seconds (temperature was dropped 0.5° C. each successive cycle), 72° C. for 2.5 minutes, followed by 16 cycles of 95° C. for 15 seconds, 58° C. for 15 seconds, and 72° C. for 2.5 minutes. An approximately 2.51 kb band corresponding to the entire coding region of CNG3B was obtained and confirmed by sequencing.

Figure 1:
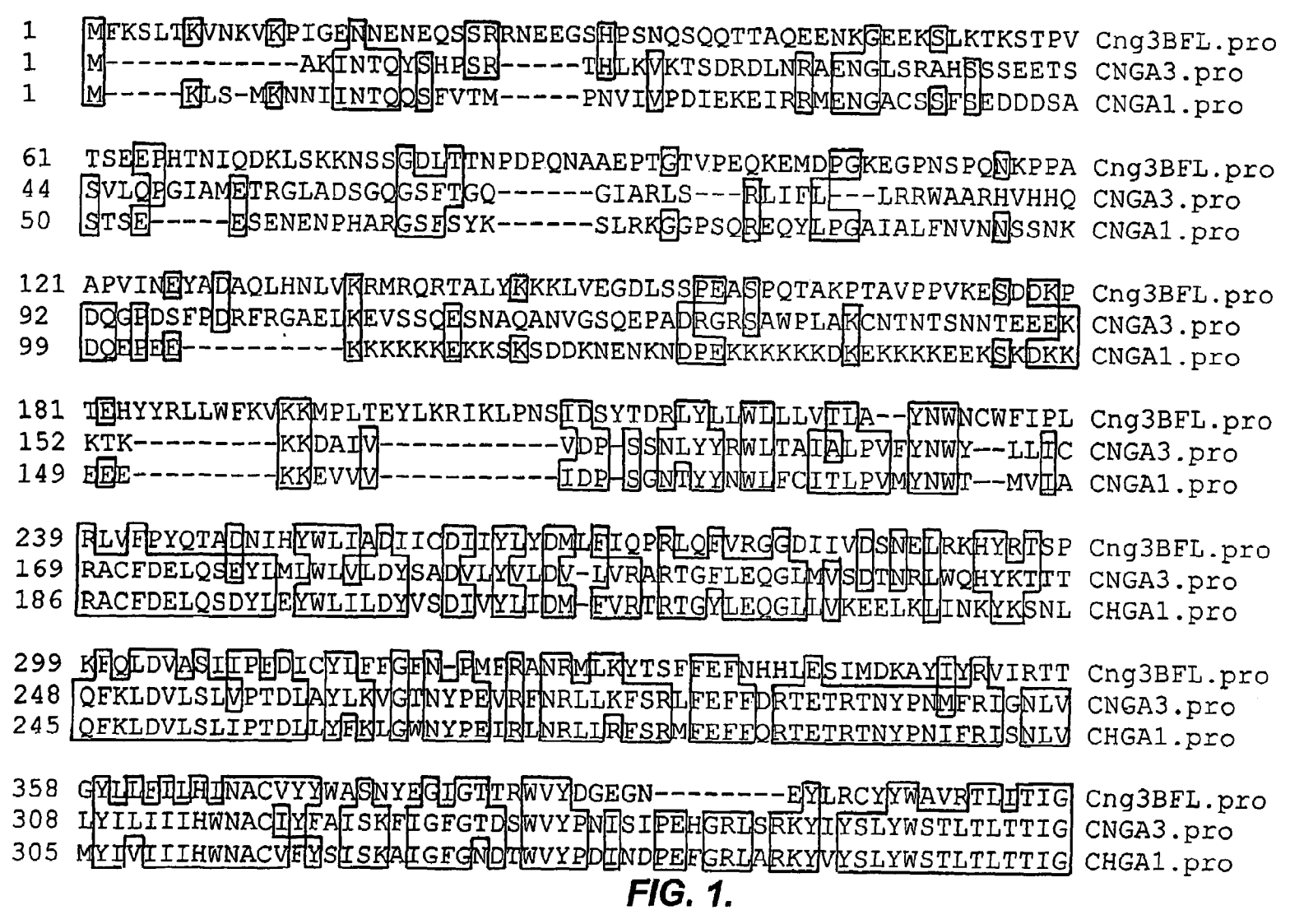

An alignment of the deduced amino acid sequence of CNG3B to previously cloned human cyclic nucleotide-gated channels (CNGA1 and CNGA3) is shown below in FIG. 1. This alignment shows regions which can be used to define the CNG species. For example, the region from amino acid 210–661 of CNG3B is 81% identical between CNG3B and mouse CNG6 (Gerstner, et al, *J Neurosci.* 20(4):1324–32 (Feb. 15, 2000)). This region of amino acids includes transmembrane domains, pore domains, and CNG binding domains.

What is claimed is:

1. An isolated nucleic acid encoding a cyclic nucleotide-gated cation channel subunit 3B (CNG3B) polypeptide, the polypeptide:
   (i) forming, with at least one cyclic nucleotide-gated channel (CNG) alpha subunit, a cation channel having the characteristic of cyclic nucleotide-gating; and
   (ii) comprising a subsequence that has at least 95% amino acid sequence identity to SEQ ID NO:1.

2. The nucleic acid of claim 1, wherein the nucleic acid encodes a polypeptide comprising the amino acid sequence of SEQ ID NO:1.

3. The nucleic acid of claim 1, wherein the nucleic acid comprises the nucleotide sequence of SEQ ID NO:2 or SEQ ID NO:3.

4. An expression vector comprising the nucleic acid of claim 1.

5. An isolated host cell transfected with the vector of claim 4.

* * * * *

SEQUENCE LISTING

<160> NUMBER OF SEQ ID NOS: 16

<210> SEQ ID NO 1
<211> LENGTH: 809
<212> TYPE: PRT
<213> ORGANISM: Homo sapiens
<220> FEATURE:
<223> OTHER INFORMATION: human cyclic nucleotide-gated cation channel
      (CNG) 3B (CNG3B)

<400> SEQUENCE: 1

Met Phe Lys Ser Leu Thr Lys Val Asn Lys Val Lys Pro Ile Gly Glu
 1               5                  10                  15

Asn Asn Glu Asn Glu Gln Ser Ser Arg Arg Asn Glu Glu Gly Ser His
             20                  25                  30

Pro Ser Asn Gln Ser Gln Gln Thr Thr Ala Gln Glu Glu Asn Lys Gly
         35                  40                  45

Glu Glu Lys Ser Leu Lys Thr Lys Ser Thr Pro Val Thr Ser Glu Glu
     50                  55                  60

Pro His Thr Asn Ile Gln Asp Lys Leu Ser Lys Lys Asn Ser Ser Gly
 65                  70                  75                  80

Asp Leu Thr Thr Asn Pro Asp Pro Gln Asn Ala Ala Glu Pro Thr Gly
                 85                  90                  95

Thr Val Pro Glu Gln Lys Glu Met Asp Pro Gly Lys Glu Gly Pro Asn

```
                     100                 105                 110
     Ser Pro Gln Asn Lys Pro Ala Ala Pro Val Ile Asn Glu Tyr Ala
                 115                 120                 125
     Asp Ala Gln Leu His Asn Leu Val Lys Arg Met Arg Gln Arg Thr Ala
             130                 135                 140
     Leu Tyr Lys Lys Leu Val Glu Gly Asp Leu Ser Pro Glu Ala
     145                 150                 155                 160
     Ser Pro Gln Thr Ala Lys Pro Thr Ala Val Pro Val Lys Glu Ser
                     165                 170                 175
     Asp Asp Lys Pro Thr Glu His Tyr Tyr Arg Leu Leu Trp Phe Lys Val
                 180                 185                 190
     Lys Lys Met Pro Leu Thr Glu Tyr Leu Lys Arg Ile Lys Leu Pro Asn
                     195                 200                 205
     Ser Ile Asp Ser Tyr Thr Asp Arg Leu Tyr Leu Leu Trp Leu Leu Leu
             210                 215                 220
     Val Thr Leu Ala Tyr Asn Trp Asn Cys Trp Phe Ile Pro Leu Arg Leu
     225                 230                 235                 240
     Val Phe Pro Tyr Gln Thr Ala Asp Asn Ile His Tyr Trp Leu Ile Ala
                     245                 250                 255
     Asp Ile Ile Cys Asp Ile Ile Tyr Leu Tyr Asp Met Leu Phe Ile Gln
                 260                 265                 270
     Pro Arg Leu Gln Phe Val Arg Gly Gly Asp Ile Ile Val Asp Ser Asn
                     275                 280                 285
     Glu Leu Arg Lys His Tyr Arg Thr Ser Thr Lys Phe Gln Leu Asp Val
             290                 295                 300
     Ala Ser Ile Ile Pro Phe Asp Ile Cys Tyr Leu Phe Gly Phe Asn
     305                 310                 315                 320
     Pro Met Phe Arg Ala Asn Arg Met Leu Lys Tyr Thr Ser Phe Phe Glu
                     325                 330                 335
     Phe Asn His His Leu Glu Ser Ile Met Asp Lys Ala Tyr Ile Tyr Arg
                 340                 345                 350
     Val Ile Arg Thr Thr Gly Tyr Leu Leu Phe Ile Leu His Ile Asn Ala
             355                 360                 365
     Cys Val Tyr Tyr Trp Ala Ser Asn Tyr Glu Gly Ile Gly Thr Thr Arg
     370                 375                 380
     Trp Val Tyr Asp Gly Glu Gly Asn Glu Tyr Leu Arg Cys Tyr Tyr Trp
     385                 390                 395                 400
     Ala Val Arg Thr Leu Ile Thr Ile Gly Gly Leu Pro Glu Pro Gln Thr
                     405                 410                 415
     Leu Phe Glu Ile Val Phe Gln Leu Leu Asn Phe Phe Ser Gly Val Phe
                 420                 425                 430
     Val Phe Ser Ser Leu Ile Gly Gln Met Arg Asp Val Ile Gly Ala Ala
             435                 440                 445
     Thr Ala Asn Gln Asn Tyr Phe Arg Ala Cys Met Asp Thr Ile Ala
                     450                 455                 460
     Tyr Met Asn Asn Tyr Ser Ile Pro Lys Leu Val Gln Lys Arg Val Arg
     465                 470                 475                 480
     Thr Trp Tyr Glu Tyr Thr Trp Asp Ser Gln Arg Met Leu Asp Glu Ser
                     485                 490                 495
     Asp Leu Leu Lys Thr Leu Pro Thr Thr Val Gln Leu Ala Leu Ala Ile
                 500                 505                 510
     Asp Val Asn Phe Ser Ile Ile Ser Lys Val Asp Leu Phe Lys Gly Cys
             515                 520                 525
```

```
Asp Thr Gln Met Ile Tyr Asp Met Leu Leu Arg Leu Lys Ser Val Leu
    530                 535                 540

Tyr Leu Pro Gly Asp Phe Val Cys Lys Gly Glu Ile Gly Lys Glu
545                 550                 555                 560

Met Tyr Ile Ile Lys His Gly Glu Val Gln Val Leu Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Asn Arg Arg Thr Ala Asn Val
    595                 600                 605

Val Ala His Gly Phe Ala Asn Leu Leu Thr Leu Asp Lys Lys Thr Leu
    610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
    675                 680                 685

Ala Arg Leu Leu Lys Leu Lys Arg Glu Gln Ala Ala Gln Lys Lys Glu
    690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
                725                 730                 735

Asn Glu Asp Lys Asp Lys Gly Arg Glu Pro Glu Glu Lys Pro Leu Asp
            740                 745                 750

Arg Pro Glu Cys Thr Ala Ser Pro Ile Ala Val Glu Glu Pro His
    755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Val Leu Thr
785                 790                 795                 800

Ile Glu Val Lys Glu Lys Ala Lys Gln
                805
```

<210> SEQ ID NO 2
<211> LENGTH: 2703
<212> TYPE: DNA
<213> ORGANISM: Homo sapiens
<220> FEATURE:
<223> OTHER INFORMATION: complete human CNG3B nucleotide sequence
<220> FEATURE:
<221> NAME/KEY: CDS
<222> LOCATION: (63)..(2492)
<223> OTHER INFORMATION: CNG3B

<400> SEQUENCE: 2

```
catttctcta ccttaaggca cagtcataaa tacagagggt tttcgaaacc acctcagaga      60
agatgtttaa atcgctgaca aaagtcaaca aggtgaagcc tataggagag aacaatgaga     120
atgaacaaag ttctcgtcgg aatgaagaag gctctcaccc aagtaatcag tctcagcaaa     180
ccacagcaca ggaagaaaac aaaggtgaag agaaatctct caaaaccaag tcaactccag     240
tcacgtctga agagccacac accaacatac aagacaaact ctccaagaaa aattcctctg     300
```

-continued

```
gagatctgac cacaaaccct gaccctcaaa atgcagcaga accaactgga acagtgccag      360
agcagaagga aatggacccc gggaagaag gtccaaacag cccacaaaac aaaccgcctg       420
cagctcctgt tataaatgag tatgccgatg cccagctaca caacctggtg aaaagaatgc     480
gtcaaagaac agccctctac aagaaaaagt tggtagaggg agatctctcc tcacccgaag    540
ccagcccaca aactgcaaag cccacggctg taccaccagt aaaagaaagc gatgataagc    600
caacagaaca ttactacagg ctgttgtggt tcaaagtcaa aaagatgcct ttaacagagt    660
acttaaagcg aattaaactt ccaaacagca tagattcata cacagatcga ctctatctcc   720
tgtggctctt gcttgtcact cttgcctata actggaactg ctggtttata ccactgcgcc   780
tcgtcttccc atatcaaacc gcagacaaca tacactactg gcttattgcg gacatcatat    840
gtgatatcat ctacctttat gatatgctat ttatccagcc cagactccag tttgtaagag    900
gaggagacat aatagtggat tcaaatgagc taaggaaaca ctacaggact tctacaaaat   960
ttcagttgga tgtcgcatca ataataccat ttgatatttg ctacctcttc tttgggttta   1020
atccaatgtt tagagcaaat aggatgttaa agtacacttc attttttgaa tttaatcatc   1080
acctagagtc tataatggac aaagcatata tctacagagt tattcgaaca actggatact   1140
tgctgtttat tctgcacatt aatgcctgtg tttattactg ggcttcaaac tatgaaggaa   1200
ttggcactac tagatgggtg tatgatgggg aaggaaacga gtatctgaga tgttattatt    1260
gggcagttcg aactttaatt accattggtg gccttccaga accacaaact ttatttgaaa   1320 ttgttttca actcttgaat ttttttttctg gagtttttgt gttctccagt ttaattggtc    1380
agatgagaga tgtgattgga gcagctacag ccaatcagaa ctacttccgc gcctgcatgg    1440
atgacaccat tgcctacatg aacaattact ccattcctaa acttgtgcaa agcgagttc    1500 ggacttggta tgaatataca tgggactctc aaagaatgct agatgagtct gatttgctta   1560
agaccctacc aactacggtc cagttagccc tcgccattga tgtgaacttc agcatcatca   1620
gcaaagtcga cttgttcaag ggttgtgata cacagatgat ttatgacatg ttgctaagat   1680
tgaaatccgt tctctatttg cctggtgact ttgtctgcaa aaagggagaa attggcaagg    1740
aaatgtatat catcaagcat ggagaagtcc aagttcttgg aggccctgat ggtactaaag    1800
ttctggttac tctgaaagct gggtcggtgt ttggagaaat cagccttcta gcagcaggag    1860
gaggaaaccg tcgaactgcc aatgtggtgg cccacggggtt tgccaatctt ttaactctag   1920
acaaaaagac cctccaagaa attctagtgc attatccaga ttctgaaagg atcctcatga    1980
agaaagccag agtgcttta aagcagaagg ctaagaccgc agaagcaacc cctccaagaa    2040
aagatcttgc cctcctcttc ccaccgaaag aagagacacc caaactgttt aaaactctcc    2100
taggaggcac aggaaaagca agtcttgcaa gactactcaa attgaagcga gagcaagcag   2160
ctcagaagaa agaaaattct gaaggaggag aggaagaagg aaaagaaaat gaagataaac   2220
aaaaagaaaa tgaagataaa caaaaagaaa atgaagataa aggaaaagaa aatgaagata   2280
aagataaagg aagagagcca gaagagaagc cactggacag acctgaatgt acagcaagtc   2340
ctattgcagt ggaggaagaa ccccactcag ttagaaggac agttttaccc agagggactt   2400
ctcgtcaatc actcattatc agcatggctc cttctgctga gggcggagaa gaggttctta    2460
ctattgaagt caaagaaaag gctaagcaat aaatgtttga ttatctttag atgtgatata   2520
gctagttccc aaagtgattg tacctaggat tgtaacttaa attaacgagg ggaaacgaca    2580
tgctgggacc cttgagaaac gaaaggcaaa tccctagctt agtttctagg acttatctga    2640
gagtgtgatt tcatgcagtg gtaataagaa gattattaaa agcaaaaaaa aaaaaaaaaa    2700
``` aaa 2703

<210> SEQ ID NO 3
<211> LENGTH: 2430
<212> TYPE: DNA
<213> ORGANISM: Homo sapiens
<220> FEATURE:
<223> OTHER INFORMATION: human CNG3B coding sequence
<220> FEATURE:
<221> NAME/KEY: CDS
<222> LOCATION: (1)..(2430)
<223> OTHER INFORMATION: CNG3B

<400> SEQUENCE: 3

| | | | | | |
|---|---|---|---|---|---|
| atgtttaaat | cgctgacaaa | agtcaacaag | gtgaagccta | taggagagaa | caatgagaat | 60 |
| gaacaaagtt | ctcgtcggaa | tgaagaaggc | tctcacccaa | gtaatcagtc | tcagcaaacc | 120 |
| acagcacagg | aagaaaacaa | aggtgaagag | aaatctctca | aaaccaagtc | aactccagtc | 180 |
| acgtctgaag | agccacacac | caacatacaa | gacaaactct | ccaagaaaaa | ttcctctgga | 240 |
| gatctgacca | aaaccctga | ccctcaaaat | gcagcagaac | caactggaac | agtgccagag | 300 |
| cagaaggaaa | tggaccccgg | gaagaaggt | ccaaacagcc | cacaaaacaa | accgcctgca | 360 |
| gctcctgtta | taaatgagta | tgccgatgcc | cagctacaca | acctggtgaa | agaatgcgt | 420 |
| caaagaacag | ccctctacaa | gaaaagttg | gtagagggag | atctctcctc | acccgaagcc | 480 |
| agcccacaaa | ctgcaaagcc | cacggctgta | ccaccagtaa | agaaaagcga | tgataagcca | 540 |
| acagaacatt | actacaggct | gttgtggttc | aaagtcaaaa | agatgccttt | aacagagtac | 600 |
| ttaaagcgaa | ttaaacttcc | aaacagcata | gattcataca | cagatcgact | ctatctcctg | 660 |
| tggctcttgc | ttgtcactct | tgcctataac | tggaactgct | ggtttatacc | actgcgcctc | 720 |
| gtcttcccat | atcaaaccgc | agacaacata | cactactggc | ttattgcgga | catcatatgt | 780 |
| gatatcatct | acctttatga | tatgctattt | atccagccca | gactccagtt | tgtaagagga | 840 |
| ggagacataa | tagtggattc | aaatgagcta | aggaaacact | acaggacttc | tacaaaattt | 900 |
| cagttggatg | tcgcatcaat | aataccattt | gatatttgct | acctcttctt | tgggttaat | 960 |
| ccaatgttta | gagcaaatag | gatgttaaag | tacacttcat | tttttgaatt | taatcatcac | 1020 |
| ctagagtcta | taatgacaa | agcatatatc | tacagagtta | ttcgaacaac | tggatacttg | 1080 |
| ctgtttattc | tgcacattaa | tgcctgtgtt | tattactggg | cttcaaacta | tgaaggaatt | 1140 |
| ggcactacta | gatgggtgta | tgatggggaa | ggaaacgagt | atctgagatg | ttattattgg | 1200 |
| gcagttcgaa | cttttaattac | cattggtggc | cttccagaac | cacaaacttt | atttgaaatt | 1260 |
| gtttttcaac | tcttgaattt | tttttctgga | gtttttgtgt | tctccagttt | aattggtcag | 1320 |
| atgagagatg | tgattggagc | agctacagcc | aatcagaact | acttccgcgc | ctgcatggat | 1380 |
| gacaccattg | cctacatgaa | caattactcc | attcctaaac | ttgtgcaaaa | gcagagttcgg | 1440 |
| acttggtatg | aatatacatg | ggactctcaa | agaatgctag | atgagtctga | tttgcttaag | 1500 |
| accctaccaa | ctacggtcca | gttagccctc | gccattgatg | tgaacttcag | catcatcagc | 1560 |
| aaagtcgact | tgttcaaggg | ttgtgataca | cagatgattt | atgacatgtt | gctaagattg | 1620 |
| aaatccgttc | tctatttgcc | tggtgacttt | gtctgcaaaa | agggagaaat | tggcaaggaa | 1680 |
| atgtatatca | tcaagcatgg | agaagtccaa | gttcttggag | gccctgatgg | tactaaagtt | 1740 |
| ctggttactc | tgaagctgg | gtcggtgttt | ggagaaatca | gccttctagc | agcaggagga | 1800 |
| ggaaaccgtc | gaactgccaa | tgtggtggcc | cacgggtttg | ccaatctttt | aactctagac | 1860 |

```
aaaaagaccc tccaagaaat tctagtgcat tatccagatt ctgaaaggat cctcatgaag    1920
aaagccagag tgcttttaaa gcagaaggct aagaccgcag aagcaacccc tccaagaaaa    1980
gatcttgccc tcctcttccc accgaaagaa gagacaccca aactgtttaa aactctccta    2040
ggaggcacag gaaaagcaag tcttgcaaga ctactcaaat tgaagcgaga gcaagcagct    2100
cagaagaaag aaaattctga aggaggagag gaagaaggaa aagaaaatga agataaacaa    2160
aaagaaaatg aagataaaca aaaagaaaat gaagataaag gaaaagaaaa tgaagataaa    2220
gataaaggaa gagagccaga agagaagcca ctggacagac ctgaatgtac agcaagtcct    2280
attgcagtgg aggaagaacc ccactcagtt agaaggacag ttttacccag agggacttct    2340
cgtcaatcac tcattatcag catggctcct tctgctgagg gcggagaaga ggttcttact    2400
attgaagtca agaaaaggc taagcaataa                                      2430
```

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence:Oligo 1
    5'-(1) sense strand primer

<400> SEQUENCE: 4
tctatctcct gtggctcttg cttgtc                                         26

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:Oligo 2
    5'-(2) antisense strand primer

<400> SEQUENCE: 5
gagtctgggc tggataaata gcatatc                                        27

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence:Oligo 3
    5'-(3) sense strand primer

<400> SEQUENCE: 6
aggaattggc actactagat gggtg                                          25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:Oligo 4
    5'-(4) antisense strand primer

<400> SEQUENCE: 7
ttcatgagga cctttcaga atctgg                                          26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:Oligo 5

5'-(5) sense strand primer

<400> SEQUENCE: 8
ggaaaccgtc gaactgccaa tgtggt     26

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence:Oligo 6
     5'-(6) sense strand primer

<400> SEQUENCE: 9
cgggtttgcc aatcttttaa ctctagac     28

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:Oligo 7
     5'-(7) antisense strand primer

<400> SEQUENCE: 10
gtccgcaata agccagtagt gtatg     25

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence:Oligo 8
     5'-(8) sense strand primer

<400> SEQUENCE: 11
tgacaagctt ccgccatgtt taaatcgctg acaaaagtc     39

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence:Oligo 9
     5'-(9) antisense strand primer

<400> SEQUENCE: 12
tgacgaattc tcccagcatg tcgtttcccc tcgttaa     37

<210> SEQ ID NO 13
<211> LENGTH: 809
<212> TYPE: PRT
<213> ORGANISM: Homo sapiens
<220> FEATURE:
<223> OTHER INFORMATION: CNG3B

<400> SEQUENCE: 13

Met Phe Lys Ser Leu Thr Lys Val Asn Lys Val Lys Pro Ile Gly Glu
 1               5                  10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Ser Thr Pro Val Thr Ser Glu Glu
    50                  55                  60

-continued

```
Pro His Thr Asn Ile Gln Asp Lys Leu Ser Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu Leu
210                 215                 220

Val Thr Leu Ala Tyr Asn Trp Asn Cys Trp Phe Ile Pro Leu Arg Leu
225                 230                 235                 240

Val Phe Pro Tyr Gln Thr Ala Asp Asn Ile His Tyr Trp Leu Ile Ala
            245                 250                 255

Asp Ile Ile Cys Asp Ile Ile Tyr Leu Tyr Asp Met Leu Phe Ile Gln
            260                 265                 270

Pro Arg Leu Gln Phe Val Arg Gly Gly Asp Ile Ile Val Asp Ser Asn
        275                 280                 285

Glu Leu Arg Lys His Tyr Arg Thr Ser Pro Lys Phe Gln Leu Asp Val
290                 295                 300

Ala Ser Ile Ile Pro Phe Asp Ile Cys Tyr Leu Phe Gly Phe Asn
305                 310                 315                 320

Pro Met Phe Arg Ala Asn Arg Met Leu Lys Tyr Thr Ser Phe Phe Glu
            325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
        355                 360                 365

Cys Val Tyr Tyr Trp Ala Ser Asn Tyr Glu Gly Ile Gly Thr Thr Arg
370                 375                 380

Trp Val Tyr Asp Gly Glu Gly Asn Glu Tyr Leu Arg Cys Tyr Tyr Trp
385                 390                 395                 400

Ala Val Arg Thr Leu Ile Thr Ile Gly Gly Leu Pro Glu Pro Gln Thr
            405                 410                 415

Leu Phe Glu Ile Val Phe Gln Leu Leu Asn Phe Phe Ser Gly Val Phe
        420                 425                 430

Val Phe Ser Ser Leu Ile Gly Gln Met Arg Asp Val Ile Gly Ala Ala
            435                 440                 445

Thr Ala Asn Gln Asn Tyr Phe Arg Ala Cys Met Asp Asp Thr Ile Ala
    450                 455                 460

Tyr Met Asn Asn Tyr Ser Ile Pro Lys Leu Val Gln Lys Arg Val Arg
465                 470                 475                 480
```

```
Thr Trp Tyr Glu Tyr Thr Trp Asp Ser Gln Arg Met Leu Asp Glu Ser
            485                 490                 495

Asp Leu Leu Lys Thr Leu Pro Thr Thr Val Gln Leu Ala Leu Ala Ile
            500                 505                 510

Asp Val Asn Phe Ser Ile Ile Ser Lys Val Asp Leu Phe Lys Gly Cys
            515                 520                 525

Asp Thr Gln Met Ile Tyr Asp Met Leu Leu Arg Leu Lys Ser Val Leu
            530                 535                 540

Tyr Leu Pro Gly Asp Phe Val Cys Lys Lys Gly Glu Ile Gly Lys Glu
545                 550                 555                 560

Met Tyr Ile Ile Lys His Gly Glu Val Gln Val Leu Gly Gly Pro Asp
                565                 570                 575

Gly Thr Lys Val Leu Val Thr Leu Lys Ala Gly Ser Val Phe Gly Glu
            580                 585                 590

Ile Ser Leu Leu Ala Ala Gly Gly Gly Asn Arg Arg Thr Ala Asn Val
            595                 600                 605

Val Ala His Gly Phe Ala Asn Leu Leu Thr Leu Asp Lys Lys Thr Leu
            610                 615                 620

Gln Glu Ile Leu Val His Tyr Pro Asp Ser Glu Arg Ile Leu Met Lys
625                 630                 635                 640

Lys Ala Arg Val Leu Leu Lys Gln Lys Ala Lys Thr Ala Glu Ala Thr
                645                 650                 655

Pro Pro Arg Lys Asp Leu Ala Leu Leu Phe Pro Pro Lys Glu Glu Thr
            660                 665                 670

Pro Lys Leu Phe Lys Thr Leu Leu Gly Gly Thr Gly Lys Ala Ser Leu
            675                 680                 685

Ala Arg Leu Leu Lys Leu Lys Arg Glu Gln Ala Ala Gln Lys Lys Glu
690                 695                 700

Asn Ser Glu Gly Gly Glu Glu Gly Lys Glu Asn Glu Asp Lys Gln
705                 710                 715                 720

Lys Glu Asn Glu Asp Lys Gln Lys Glu Asn Glu Asp Lys Gly Lys Glu
            725                 730                 735

Asn Glu Asp Lys Asp Lys Gly Arg Glu Pro Glu Lys Pro Leu Asp
            740                 745                 750

Arg Pro Glu Cys Thr Ala Ser Pro Ile Ala Val Glu Glu Pro His
            755                 760                 765

Ser Val Arg Arg Thr Val Leu Pro Arg Gly Thr Ser Arg Gln Ser Leu
770                 775                 780

Ile Ile Ser Met Ala Pro Ser Ala Glu Gly Gly Glu Val Leu Thr
785                 790                 795                 800

Ile Glu Val Lys Glu Lys Ala Lys Gln
            805

<210> SEQ ID NO 14
<211> LENGTH: 694
<212> TYPE: PRT
<213> ORGANISM: Homo sapiens
<220> FEATURE:
<223> OTHER INFORMATION: CNGA1

<400> SEQUENCE: 14

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30
```

-continued

```
Ser Arg Ala His Ser Ser Glu Glu Thr Ser Ser Val Leu Gln Pro
         35                  40                  45

Gly Ile Ala Met Glu Thr Arg Gly Leu Ala Asp Ser Gly Gln Gly Ser
 50                  55                  60

Phe Thr Gly Gln Gly Ile Ala Arg Leu Ser Arg Leu Ile Phe Leu Leu
 65                  70                  75                  80

Arg Arg Trp Ala Ala Arg His Val His His Gln Asp Gln Gly Pro Asp
                 85                  90                  95

Ser Phe Pro Asp Arg Phe Arg Gly Ala Glu Leu Lys Glu Val Ser Ser
                100                 105                 110

Gln Glu Ser Asn Ala Gln Ala Asn Val Gly Ser Gln Glu Pro Ala Asp
                115                 120                 125

Arg Gly Arg Ser Ala Trp Pro Leu Ala Lys Cys Asn Thr Asn Thr Ser
        130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
                180                 185                 190

Asp Glu Leu Gln Ser Glu Tyr Leu Met Leu Trp Leu Val Leu Asp Tyr
                195                 200                 205

Ser Ala Asp Val Leu Tyr Val Leu Asp Val Leu Val Arg Ala Arg Thr
        210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
                260                 265                 270

Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
        290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr
                340                 345                 350

Ile Tyr Ser Leu Tyr Trp Ser Thr Leu Thr Leu Thr Thr Ile Gly Glu
        355                 360                 365

Thr Pro Pro Pro Val Lys Asp Glu Glu Tyr Leu Phe Val Val Val Asp
370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
                420                 425                 430

Leu Glu Thr Arg Val Ile Arg Trp Phe Asp Tyr Leu Trp Ala Asn Lys
        435                 440                 445

Lys Thr Val Asp Glu Lys Glu Val Leu Lys Ser Leu Pro Asp Lys Leu
```

-continued

```
              450                 455                 460
Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
                500                 505                 510

Gly Asp Ile Gly Lys Glu Met Tyr Ile Ile Asn Glu Gly Lys Leu Ala
                515                 520                 525

Val Val Ala Asp Asp Gly Val Thr Gln Phe Val Val Leu Ser Asp Gly
530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
                580                 585                 590

Glu Ala Lys Lys Ala Leu Glu Glu Lys Gly Arg Gln Ile Leu Met Lys
                595                 600                 605

Asp Asn Leu Ile Asp Glu Glu Leu Ala Arg Ala Gly Ala Asp Pro Lys
                610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
                660                 665                 670

Gly Asp Lys Pro Leu Ala Asp Gly Glu Val Pro Gly Asp Ala Thr Lys
                675                 680                 685

Thr Glu Asp Lys Gln Gln
                690

<210> SEQ ID NO 15
<211> LENGTH: 690
<212> TYPE: PRT
<213> ORGANISM: Homo sapiens
<220> FEATURE:
<223> OTHER INFORMATION: CNGA3

<400> SEQUENCE: 15

Met Lys Leu Ser Met Lys Asn Ile Ile Asn Thr Gln Gln Ser Phe
  1               5                  10                  15

Val Thr Met Pro Asn Val Ile Val Pro Asp Ile Glu Lys Glu Ile Arg
                 20                  25                  30

Arg Met Glu Asn Gly Ala Cys Ser Ser Phe Ser Glu Asp Asp Ser
                 35                  40                  45

Ala Ser Thr Ser Glu Glu Ser Glu Asn Glu Asn Pro His Ala Arg Gly
     50                  55                  60

Ser Phe Ser Tyr Lys Ser Leu Arg Lys Gly Gly Pro Ser Gln Arg Glu
65                   70                  75                  80

Gln Tyr Leu Pro Gly Ala Ile Ala Leu Phe Asn Val Asn Asn Ser Ser
                 85                  90                  95

Asn Lys Asp Gln Glu Pro Glu Glu Lys Lys Lys Lys Lys Glu Lys
                100                 105                 110

Lys Ser Lys Ser Asp Asp Lys Asn Glu Asn Lys Asn Asp Pro Glu Lys
```

```
                115                 120                 125
Lys Lys Lys Lys Lys Asp Lys Glu Lys Lys Lys Glu Glu Lys Ser
            130                 135                 140
Lys Asp Lys Lys Glu Glu Glu Lys Lys Glu Val Val Ile Asp Pro
145                 150                 155                 160
Ser Gly Asn Thr Tyr Tyr Asn Trp Leu Phe Cys Ile Thr Leu Pro Val
                165                 170                 175
Met Tyr Asn Trp Thr Met Val Ile Ala Arg Ala Cys Phe Asp Glu Leu
            180                 185                 190
Gln Ser Asp Tyr Leu Glu Tyr Trp Leu Ile Leu Asp Tyr Val Ser Asp
        195                 200                 205
Ile Val Tyr Leu Ile Asp Met Phe Val Arg Thr Arg Thr Gly Tyr Leu
        210                 215                 220
Glu Gln Gly Leu Leu Val Lys Glu Glu Leu Lys Leu Ile Asn Lys Tyr
225                 230                 235                 240
Lys Ser Asn Leu Gln Phe Lys Leu Asp Val Leu Ser Leu Ile Pro Thr
                245                 250                 255
Asp Leu Leu Tyr Phe Lys Leu Gly Trp Asn Tyr Pro Glu Ile Arg Leu
            260                 265                 270
Asn Arg Leu Leu Arg Phe Ser Arg Met Phe Glu Phe Phe Gln Arg Thr
        275                 280                 285
Glu Thr Arg Thr Asn Tyr Pro Asn Ile Phe Arg Ile Ser Asn Leu Val
        290                 295                 300
Met Tyr Ile Val Ile Ile His Trp Asn Ala Cys Val Phe Tyr Ser
305                 310                 315                 320
Ile Ser Lys Ala Ile Gly Phe Gly Asn Asp Thr Trp Val Tyr Pro Asp
                325                 330                 335
Ile Asn Asp Pro Glu Phe Gly Arg Leu Ala Arg Lys Tyr Val Tyr Ser
            340                 345                 350
Leu Tyr Trp Ser Thr Leu Thr Leu Thr Thr Ile Gly Glu Thr Pro Pro
        355                 360                 365
Pro Val Arg Asp Ser Glu Tyr Val Phe Val Val Asp Phe Leu Ile
        370                 375                 380
Gly Val Leu Ile Phe Ala Thr Ile Val Gly Asn Ile Gly Ser Met Ile
385                 390                 395                 400
Ser Asn Met Asn Ala Ala Arg Ala Glu Phe Gln Ala Arg Ile Asp Ala
                405                 410                 415
Ile Lys Gln Tyr Met His Phe Arg Asn Val Ser Lys Asp Met Glu Lys
            420                 425                 430
Arg Val Ile Lys Trp Phe Asp Tyr Leu Trp Thr Asn Lys Lys Thr Val
        435                 440                 445
Asp Glu Lys Glu Val Leu Lys Tyr Leu Pro Asp Lys Leu Arg Ala Glu
        450                 455                 460
Ile Ala Ile Asn Val His Leu Asp Thr Leu Lys Lys Val Arg Ile Phe
465                 470                 475                 480
Ala Asp Cys Glu Ala Gly Leu Leu Val Glu Leu Val Leu Lys Leu Gln
                485                 490                 495
Pro Gln Val Tyr Ser Pro Gly Asp Tyr Ile Cys Lys Lys Gly Asp Ile
            500                 505                 510
Gly Arg Glu Met Tyr Ile Ile Lys Glu Gly Lys Leu Ala Val Val Ala
        515                 520                 525
Asp Asp Gly Val Thr Gln Phe Val Val Leu Ser Asp Gly Ser Tyr Phe
        530                 535                 540
```

-continued

```
Gly Glu Ile Ser Ile Leu Asn Ile Lys Gly Ser Lys Ala Gly Asn Arg
545                 550                 555                 560

Arg Thr Ala Asn Ile Lys Ser Ile Gly Tyr Ser Asp Leu Phe Cys Leu
                565                 570                 575

Ser Lys Asp Asp Leu Met Glu Ala Leu Thr Glu Tyr Pro Asp Ala Lys
            580                 585                 590

Thr Met Leu Glu Glu Lys Gly Lys Gln Ile Leu Met Lys Asp Gly Leu
        595                 600                 605

Leu Asp Leu Asn Ile Ala Asn Ala Gly Ser Asp Pro Lys Asp Leu Glu
    610                 615                 620

Glu Lys Val Thr Arg Met Glu Gly Ser Val Asp Leu Leu Gln Thr Arg
625                 630                 635                 640

Phe Ala Arg Ile Leu Ala Glu Tyr Glu Ser Met Gln Gln Lys Leu Lys
                645                 650                 655

Gln Arg Leu Thr Lys Val Glu Lys Phe Leu Lys Pro Leu Ile Asp Thr
            660                 665                 670

Glu Phe Ser Ser Ile Glu Gly Pro Gly Ala Glu Ser Gly Pro Ile Asp
        675                 680                 685

Ser Thr
    690
```

```
<210> SEQ ID NO 16
<211> LENGTH: 2757
<212> TYPE: DNA
<213> ORGANISM: Homo sapiens
<220> FEATURE:
<223> OTHER INFORMATION: complete CNG3B sequence derived from assembly
      of PCR fragments
<220> FEATURE:
<221> NAME/KEY: CDS
<222> LOCATION: (112)..(2541)
<223> OTHER INFORMATION: CNG3B

<400> SEQUENCE: 16
ccatcctaat acgactcact atagggctcg agcggccgcc cgggcaggtc atttctctac      60
cttaaggcac agtcataaat acagagggtt ttcagaacca cctcagagaa gatgttttaaa   120 tcgctgacaa aagtcaacaa ggtgaagcct ataggagaga acaatgagaa tgaacaaagt    180
tctcgtcgga atgaagaagg ctctcaccca agtaatcagt ctcagcaaac cacagcacag    240
gaagaaaaca aaggtgaaga gaaatctctc aaaaccaagt caactccagt cacgtctgaa    300
gagccacaca ccaacataca agacaaactc tccaagaaaa attcctctgg agatctgacc    360
acaaaccctg accctcaaaa tgcagcagaa ccaactggaa cagtgccaga gcagaaggaa    420
atggaccccg ggaagaagg tccaaacagc ccacaaaaca aaccgcctgc agctcctgtt     480
ataaatgagt atgccgatgc ccagctacac aacctggtga aagaatgcg tcaaagaaca     540 gccctctaca agaaaaagtt ggtagaggga gatctctcct cacccgaagc cagcccacaa    600
actgcaaagc ccacggctgt accaccagta aagaaagcg atgataagcc aacagaacat    660
tactacaggc tgttgtggtt caaagtcaaa aagatgcctt taacagagta cttaaagcga    720
attaaacttc caaacagcat agattcatac acagatcgac tctatctcct gtggctcttg    780
cttgtcactc ttgcctataa ctggaactgc tggtttatac cactgcgcct cgtcttccca    840
tatcaaaccg cagacaacat acactactgg cttattgcgg acatcatatg tgatatcatc    900
tacctttatg atatgctatt tatccagccc agactccagt tgtaagagg aggagacata    960 atagtggatt caaatgagct aaggaaacac tacaggactt ctacaaaatt tcagttggat   1020
```

-continued

```
gtcgcatcaa taataccatt tgatatttgc tacctcttct ttgggtttaa tccaatgttt    1080
agagcaaata ggatgttaaa gtacacttca tttttgaat ttaatcatca cctagagtct    1140
ataatggaca aagcatatat ctacagagtt attcgaacaa ctggatactt gctgtttatt    1200
ctgcacatta atgcctgtgt ttattactgg gcttcaaact atgaaggaat tggcactact    1260
agatgggtgt atgatgggga aggaaacgag tatctgagat gttattattg ggcagttcga    1320
actttaatta ccattggtgg ccttccagaa ccacaaactt tatttgaaat tgtttttcaa    1380
ctcttgaatt ttttttctgg agtttttgtg ttctccagtt taattggtca gatgagagat    1440
gtgattggag cagctacagc caatcagaac tacttccgcg cctgcatgga tgacaccatt    1500
gcctacatga acaattactc cattcctaaa cttgtgcaaa agcgagttcg gacttggtat    1560
gaatatacat gggactctca aagaatgcta gatgagtctg atttgcttaa gaccctacca    1620
actacggtcc agttagccct cgccattgat gtgaacttca gcatcatcag caaagtcgac    1680
ttgttcaagg gttgtgatac acagatgatt tatgacatgt tgctaagatt gaaatccgtt    1740
ctctatttgc ctggtgactt tgtctgcaaa aagggagaaa ttggcaagga aatgtatatc    1800
atcaagcatg gagaagtcca agttcttgga ggccctgatg gtactaaagt tctggttact    1860
ctgaaagctg ggtcggtgtt tggagaaatc agccttctag cagcaggagg aggaaaccgt    1920
cgaactgcca atgtggtggc ccacgggttt gccaatcttt taactctaga caaaaagacc    1980
ctccaagaaa ttctagtgca ttatccagat tctgaaagga tcctcatgaa gaaagccaga    2040
gtgcttttaa agcagaaggc taagaccgca gaagcaaccc ctccaagaaa agatcttgcc    2100
ctcctcttcc caccgaaaga agagacaccc aaactgttta aaactctcct aggaggcaca    2160
ggaaaagcaa gtcttgcaag actactcaaa ttgaagcgag agcaagcagc tcagaagaaa    2220
gaaaattctg aaggaggaga ggaagaagga aaagaaaatg aagataaaca aaaagaaaat    2280
gaagataaac aaaaagaaaa tgaagataaa ggaaaagaaa atgaagataa agataaagga    2340
agagagccag aagagaagcc actggacaga cctgaatgta cagcaagtcc tattgcagtg    2400
gaggaagaac cccactcagt tagaaggaca gttttaccca gagggacttc tcgtcaatca    2460
ctcattatca gcatggctcc ttctgctgag ggcggagaag aggttcttac tattgaagtc    2520
aaagaaaagg ctaagcaata aatgtttgat tatctttaga tgtgatatag ctagttccca    2580
aagtgattgt acctaggatt gtaacttaaa ttaacgaggg gaaacgacat gctgggaccc    2640
ttgagaaacg aaaggcaaat ccctagctta gtttctagga cttatctgag agtgtgattt    2700
catgcagtgg taataagaag attattaaaa gcaaaaaaaa aaaaaaaaa aaaaaaa      2757
```